(12) United States Patent
Koop et al.

(10) Patent No.: US 10,758,724 B2
(45) Date of Patent: Sep. 1, 2020

(54) IMPLANTABLE MEDICAL DEVICE DELIVERY SYSTEM WITH INTEGRATED SENSOR

(71) Applicant: CARDIAC PACEMAKERS, INC., St. Paul, MN (US)

(72) Inventors: Brendan Early Koop, Ham Lake, MN (US); Yinghong Yu, Shoreview, MN (US); Qi An, Blaine, MN (US); Keith R. Maile, New Brighton, MN (US); Pramodsingh Hirasingh Thakur, Woodbury, MN (US); Bin Mi, Plymouth, MN (US); Jeffrey E. Stahmann, Ramsey, MN (US); Viktoria A. Averina, Shoreview, MN (US); Krzysztof Z. Siejko, Maple Grove, MN (US); Michael J. Kane, St. Paul, MN (US); Allan Charles Shuros, St. Paul, MN (US); Arjun D. Sharma, St. Paul, MN (US); Brian Soltis, St. Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 282 days.

(21) Appl. No.: 15/793,149

(22) Filed: Oct. 25, 2017

(65) Prior Publication Data
US 2018/0117304 A1 May 3, 2018

Related U.S. Application Data

(60) Provisional application No. 62/413,748, filed on Oct. 27, 2016.

(51) Int. Cl.
*A61N 1/05* (2006.01)
*A61B 5/00* (2006.01)
(Continued)

(52) U.S. Cl.
CPC ............ *A61N 1/056* (2013.01); *A61B 5/0031* (2013.01); *A61B 5/686* (2013.01); *A61N 1/372* (2013.01);
(Continued)

(58) Field of Classification Search
CPC .......... B67D 1/0081; B67D 2001/0093; B67D 2001/0096; B67D 1/0882; B67D 1/0015;
(Continued)

(56) References Cited

U.S. PATENT DOCUMENTS

| | | | |
|---|---|---|---|
| 3,835,864 | A | 9/1974 | Rasor et al. |
| 3,943,936 | A | 3/1976 | Rasor et al. |

(Continued)

FOREIGN PATENT DOCUMENTS

| | | | |
|---|---|---|---|
| AU | 2008279789 | B2 | 10/2011 |
| AU | 2008329620 | B2 | 5/2014 |

(Continued)

OTHER PUBLICATIONS

US 8,886,318 B2, 11/2014, Jacobson et al. (withdrawn)
(Continued)

*Primary Examiner* — Erin M Piateski
(74) *Attorney, Agent, or Firm* — Seager, Tufte & Wickhem LLP

(57) ABSTRACT

A delivery and deployment device may include a handle assembly and a shaft extending distally from the handle assembly. A device containment housing may be coupled to a distal region of the shaft and may extend distally therefrom. The distal containment housing may be configured to accommodate at least a portion of the IMD therein. The IMD may, for example, be a leadless pacemaker, a lead, a neurostimulation device, a sensor or any other suitable IMD. A plurality of electrodes may be distributed about an exterior surface of the device containment housing such that at least (Continued)

some of the plurality of electrodes may be positioned to test a potential IMD deployment location before deploying the IMD.

17 Claims, 25 Drawing Sheets

(51) Int. Cl.
 *A61N 1/372* (2006.01)
 *A61N 1/375* (2006.01)
 *A61F 2/24* (2006.01)
 *A61N 1/37* (2006.01)

(52) U.S. Cl.
 CPC .......... *A61F 2/2436* (2013.01); *A61N 1/3706* (2013.01); *A61N 1/3756* (2013.01); *A61N 1/37288* (2013.01)

(58) Field of Classification Search
 CPC ... G01F 1/0755; G01F 15/063; A61B 5/4875; A63B 71/00; A63B 2220/72; A63B 2220/75
 USPC ......................................................... 600/31
 See application file for complete search history.

(56) References Cited

U.S. PATENT DOCUMENTS

| | | | |
|---|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |

(56) References Cited

U.S. PATENT DOCUMENTS

| | | |
|---|---|---|
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |

(56) References Cited

U.S. PATENT DOCUMENTS

| | | |
|---|---|---|
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |

(56) References Cited

U.S. PATENT DOCUMENTS

| | | |
|---|---|---|
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |

(56) References Cited

U.S. PATENT DOCUMENTS

| | | |
|---|---|---|
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,072,914 B2 | 7/2015 | Greenhut et al. |
| 9,101,281 B2 | 8/2015 | Reinert et al. |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,308,365 B2 | 4/2016 | Nordstrom et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 10,080,887 B2 | 9/2018 | Schmidt et al. |
| 10,080,888 B2 | 9/2018 | Kelly et al. |
| 10,080,900 B2 | 9/2018 | Ghosh et al. |
| 10,080,903 B2 | 9/2018 | Willis et al. |
| 10,086,206 B2 | 10/2018 | Sambelashvili |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0087089 A1 | 7/2002 | Ben-Haim |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |

(56) References Cited

U.S. PATENT DOCUMENTS

| | | |
|---|---|---|
| 2003/0045805 A1 | 3/2003 | Sheldon et al. |
| 2003/0088278 A1 | 5/2003 | Bardy et al. |
| 2003/0093131 A1* | 5/2003 | Loeb .............. A61N 1/36003 607/48 |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1* | 5/2008 | Hastings .............. A61N 1/0587 607/127 |
| 2008/0119911 A1 | 5/2008 | Rosero |
| 2008/0130670 A1 | 6/2008 | Kim et al. |
| 2008/0140142 A1* | 6/2008 | Darvish .................. A61N 1/05 607/11 |
| 2008/0147138 A1* | 6/2008 | Maskara .............. A61N 1/0587 607/18 |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |

(56) References Cited

U.S. PATENT DOCUMENTS

| | | |
|---|---|---|
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1* | 6/2011 | Markowitz .......... A61B 5/0028 607/60 |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1* | 11/2011 | Pellegrini ............ A61N 1/0573 607/9 |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1* | 7/2012 | Lee .................. A61B 17/3468 606/129 |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |

(56) References Cited

U.S. PATENT DOCUMENTS

| | | |
|---|---|---|
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172034 A1 | 6/2014 | Bornzin et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0277240 A1 | 9/2014 | Maskara et al. |
| 2014/0303704 A1 | 10/2014 | Suwito et al. |
| 2014/0309706 A1 | 10/2014 | Jacobson |
| 2014/0343348 A1* | 11/2014 | Kaplan .............. A61B 17/3478 600/8 |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0142069 A1 | 5/2015 | Sambelashvili |
| 2015/0142070 A1 | 5/2015 | Sambelashvili |
| 2015/0157861 A1 | 6/2015 | Aghassian |
| 2015/0157866 A1 | 6/2015 | Demmer et al. |
| 2015/0165199 A1 | 6/2015 | Karst et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0059024 A1 | 3/2016 | Stahmann et al. |
| 2016/0067490 A1 | 3/2016 | Carney et al. |
| 2016/0114156 A1 | 4/2016 | Haasl et al. |
| 2016/0114157 A1 | 4/2016 | Haasl et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0136440 A1 | 5/2016 | Min et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0213940 A1 | 7/2016 | Reinke et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0027463 A1* | 2/2017 | Du .................. A61B 5/04012 |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 2204127 A1 | 7/2010 |
| EP | 1904166 B1 | 6/2011 |
| EP | 2471452 A1 | 7/2012 |

(56) References Cited

FOREIGN PATENT DOCUMENTS

| | | |
|---|---|---|
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2005000206 A3 | 1/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2009006531 A1 | 1/2009 |
| WO | 2011028949 A1 | 3/2011 |
| WO | 2012054102 A1 | 4/2012 |
| WO | 2012091747 A1 | 7/2012 |
| WO | 2013080038 A2 | 6/2013 |
| WO | 2013098644 A3 | 7/2013 |
| WO | 2013184787 A1 | 12/2013 |
| WO | 2014087337 A1 | 6/2014 |
| WO | 2014120769 A1 | 8/2014 |
| WO | 2014178035 A1 | 11/2014 |

OTHER PUBLICATIONS

International Search Report and Written Opinion for Application No. PCT/US2017/058223, 21 pages, dated Apr. 13, 2018.
"Advancing Science for Life: Rhythmia Mapping System," Boston Scientific, 109 pages, 2015.
"Rhythmia Mapping System: Experience High Definition, High Resolution Mapping," Boston Scientific, 12 pages, 2015.
Invitation to Pay Additional Fees and, Where Applicable, Protest fee for Application No. PCT/US2017/058223, 14 pages, dated Jan. 22, 2018.
"Instructions for Use System 1, Leadless Cardiac Pacemaker (LCP) and Delivery Catheter," Nanostim Leadless Pacemakers, pp. 1-28, 2013.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Seyedi et al., "A Survey on Intrabody Communications for Body Area Network Application," IEEE Transactions on Biomedical Engineering, vol. 60(8): 2067-2079, 2013.
Spickler et al., "Totally Self-Contained Intracardiac Pacemaker," Journal of Electrocardiology, vol. 3(384): 324-331, 1970.
Wegmüller, "Intra-Body Communication for Biomedical Sensor Networks," Diss. ETH, No. 17323, 1-173, 2007.

\* cited by examiner

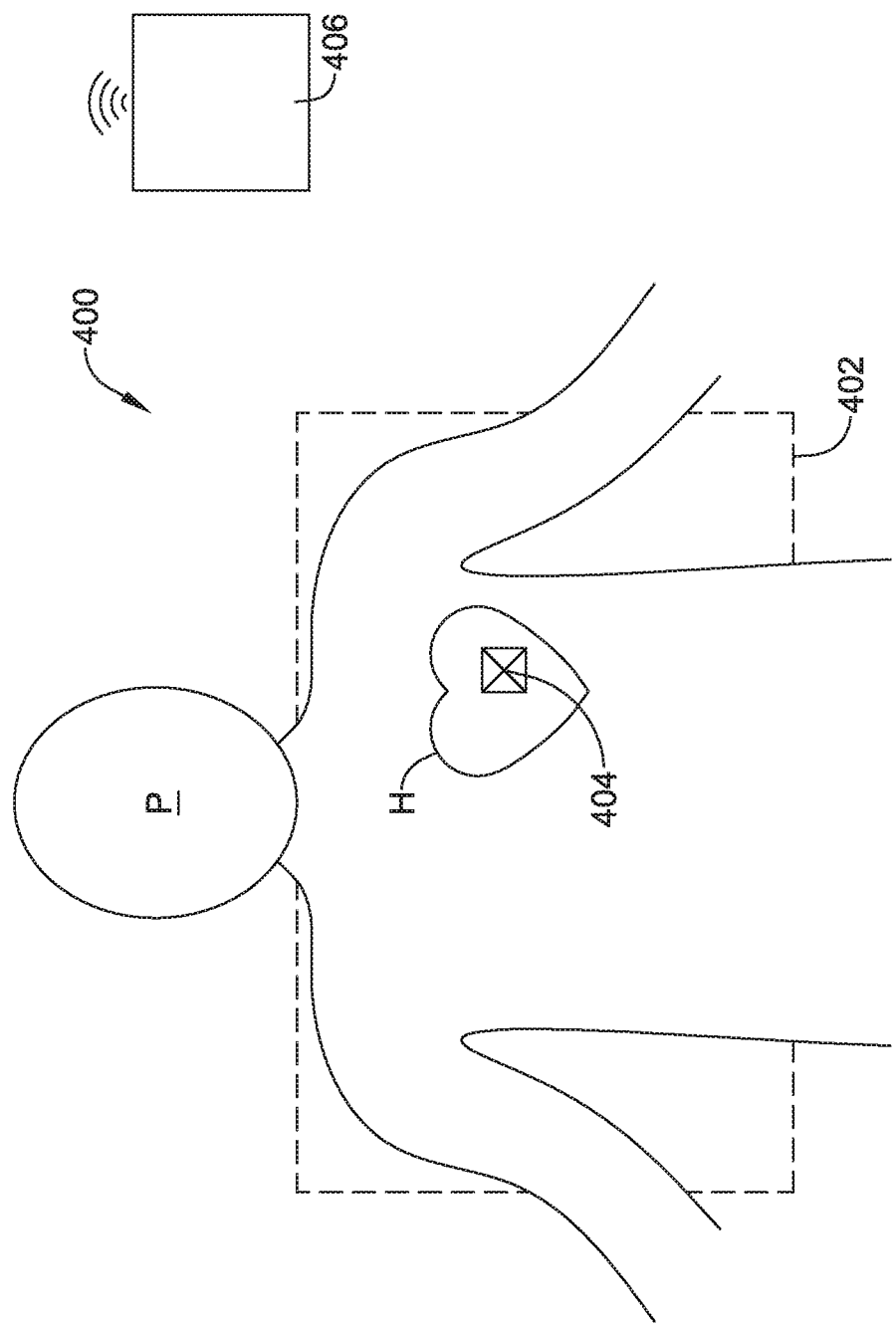

IMPLANTABLE MEDICAL DEVICE DELIVERY SYSTEM WITH INTEGRATED SENSOR

CROSS REFERENCE TO RELATED APPLICATIONS

This application claims the benefit of U.S. Provisional Patent Application Ser. No. 62/413,748 filed on Oct. 27, 2016, the disclosure of which is incorporated herein by reference.

TECHNICAL FIELD

The present disclosure pertains to medical devices, and methods for manufacturing and/or using medical devices. More particularly, the present disclosure pertains to leadless devices and methods, such as leadless cardiac pacing devices and methods, and delivery devices and methods for such leadless cardiac pacing devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

SUMMARY

This disclosure provides design, material, manufacturing method, and use alternatives for medical devices, including delivery devices.

An example delivery and deployment device that is configured to deliver an implantable medical device (IMD) to a chamber of a patient's heart and to deploy the IMD may include a handle assembly and a shaft extending distally from the handle assembly, the shaft including a distal region. A device containment housing may be coupled to the distal region of the shaft and may extend distally therefrom. The distal containment housing may be configured to accommodate at least a portion of the IMD therein. The IMD may, for example, be a leadless pacemaker, a lead, a neurostimulation device, a sensor or any other suitable IMD. A plurality of electrodes may be distributed about an exterior surface of the device containment housing such that at least some of the plurality of electrodes may be positioned to test a potential IMD deployment location before deploying the IMD. In some cases, a plurality of electrical conductors may be operably coupled with the plurality of electrodes and may extend proximally back along the shaft toward the handle assembly, the plurality of electrical conductors having proximal ends configured to be operably coupled to a testing device.

Alternatively or additionally to any of the embodiments above, the plurality of electrodes may include at least some electrodes that are radially disposed about the exterior surface of the device containment housing.

Alternatively or additionally to any of the embodiments above, the plurality of electrodes may include at least four electrodes spaced axially along the exterior surface of the device containment housing, the at least four electrodes including a first electrode, a second electrode, a third electrode and a fourth electrode. The first electrode and the fourth electrode may be spaced apart a first distance to form a stimulation dipole providing a potential difference. The second electrode and the third electrode may be spaced apart a second distance less than the first distance to provide a conductivity measurement by measuring a voltage between the second electrode and the third electrode resulting from the potential difference applied by the first electrode and the second electrode and the second electrode and the third electrode disposed between the first electrode and the fourth electrode.

Alternatively or additionally to any of the embodiments above, the plurality of electrodes may include a first electrode and a second electrode disposed on an exterior surface of the device containment housing to form a stimulation bipole.

Alternatively or additionally to any of the embodiments above, the delivery and deployment device may further include a pressure sensor configured to obtain an indication of pressure in the chamber of the patient's heart in response to a stimulating electrical pulse delivered via the first electrode and the second electrode.

Alternatively or additionally to any of the embodiments above, the pressure sensor may be disposed at or near a proximal end of the device containment housing.

Alternatively or additionally to any of the embodiments above, the delivery and deployment device may further include a first pressure sensor that is configured to obtain an indication of pressure in the chamber of the patient's heart and a second pressure sensor that is configured to obtain an indication of pressure in a different chamber of the patient's heart.

Alternatively or additionally to any of the embodiments above, the delivery and deployment device may further include an accelerometer and/or a gyroscope that is fixed relative to the device containment housing.

Alternatively or additionally to any of the embodiments above, at least some of the plurality of electrodes are disposed on an expandable assembly movably secured about an exterior of the device containment housing, the expandable assembly movable to a deployed configuration in which at least some of the plurality of electrodes contact cardiac tissue for endocardial mapping of at least part of the chamber of the patient's heart prior to IMD deployment.

Alternatively or additionally to any of the embodiments above, the delivery and deployment device further includes one or more magnet tracking sensor fixed relative to the device containment housing for tracking purposes.

An example IMD implantation device that is configured to deliver an implantable medical device (IMD) to a chamber of a patient's heart and to deploy the IMD therein may include a handle assembly and a shaft extending distally from the handle assembly, the shaft including a distal region. A device containment housing may be coupled to the distal region of the shaft and may extend distally therefrom. The distal containment housing may be configured to accommodate at least a portion of the IMD therein. A deployment member may extend through the shaft and may be configured to apply a deployment force to the IMD in order to move the IMD from the device containment housing to deploy the IMD in the patient's heart. A plurality of electrodes may be distributed about an exterior surface of the device containment housing such that at least some of the plurality of electrodes may be positioned to test a potential IMD deployment location before deploying the IMD. A plurality of electrical conductors may be operably coupled with the plurality of electrodes and may extend proximally back along the shaft toward the handle assembly, the plurality of electrical conductors having proximal ends configured to be operably coupled to a testing device.

Alternatively or additionally to any of the embodiments above, the deployment member may be a push tube, and the IMD implantation device may further include a tether that extends distally through the push tube and is coupled to the IMD, the tether configured to be used to retrieve the IMD back into the device containment housing if an alternate deployment location is desired.

Alternatively or additionally to any of the embodiments above, the plurality of electrodes may include at least four electrodes spaced axially along the device containment housing, the at least four electrodes including a first electrode, a second electrode, a third electrode and a fourth electrode. The first electrode and the fourth electrode may be spaced apart a first distance to form a stimulation dipole providing a potential difference, wherein the fourth electrode extends to a distal end of the device containment housing. The second electrode and the third electrode may be spaced apart a second distance less than the first distance to provide a conductivity measurement by measuring a voltage between the second electrode and the third electrode resulting from the potential difference applied by the first electrode and the second electrode and the second electrode and the third electrode may be disposed between the first electrode and the fourth electrode.

Alternatively or additionally to any of the embodiments above, the plurality of electrodes may include a first electrode and a second electrode that are disposed on an exterior surface of the device containment housing to form a stimulation bipole.

Alternatively or additionally to any of the embodiments above, the IMD implantation device may further include a pressure sensor that is configured to obtain an indication of pressure in the chamber of the patient's heart in response to a stimulating electrical pulse delivered via the first electrode and the second electrode.

Alternatively or additionally to any of the embodiments above, the pressure sensor may be disposed at or near a proximal end of the device containment housing.

Alternatively or additionally to any of the embodiments above, the IMD implantation device may further include an accelerometer and/or a gyroscope that is fixed relative to the device containment housing.

An example implantation device that is configured to deliver a leadless cardiac pacemaker (LCP) to a chamber of a patient's heart and to deploy the LCP therein may include a handle assembly and a shaft that extends distally from the handle assembly, the shaft including a distal region. A device containment housing may be coupled to the distal region of the shaft and may extend distally therefrom, the device containment housing configured to accommodate the LCP therein. A deployment member may extend through the shaft and may be configured to apply a deployment force to the LCP in order to move the LCP from a distal end of the device containment housing to deploy the LCP in the patient's heart. One or more tracking sensors may be fixed relative to the device containment housing to facilitate tracking of the device containment housing.

Alternatively or additionally to any of the embodiments above, the one or more tracking sensors may include a magnetic tracking sensor to facilitate magnet tracking of the device containment housing and/or an impedance tracking sensor to facilitate impedance tracking of the device containment housing.

Alternatively or additionally to any of the embodiments above, the implantation device may further include an LCP disposed within the device containment housing, and the LCP may include one or more LCP magnetic tracking sensors to facilitate magnet tracking of the LCP and/or one or more LCP impedance tracking sensors to facilitate impedance tracking of the LCP.

The above summary of some illustrative embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which:

FIG. 20 is a schematic view of an illustrative imaging system.

Figure 1:
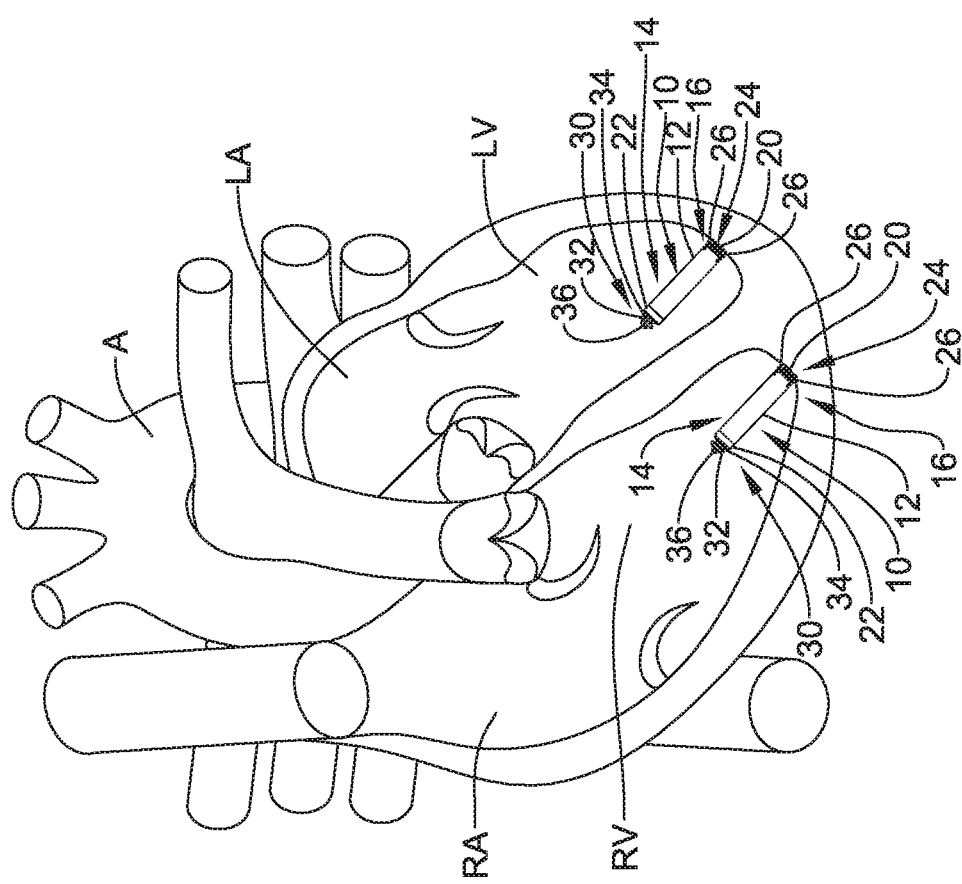
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers may include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules that may, for example, be fixed to an intracardiac implant site in a cardiac chamber. In some cases, the small capsule may include bipolar pacing/sensing electrodes, a power source (e.g. a battery), and associated electrical circuitry for controlling the pacing/sensing electrodes, and thus may provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle. Accordingly, it may be desirable to provide delivery devices which facilitate advancement through the vasculature.

Figure 2:
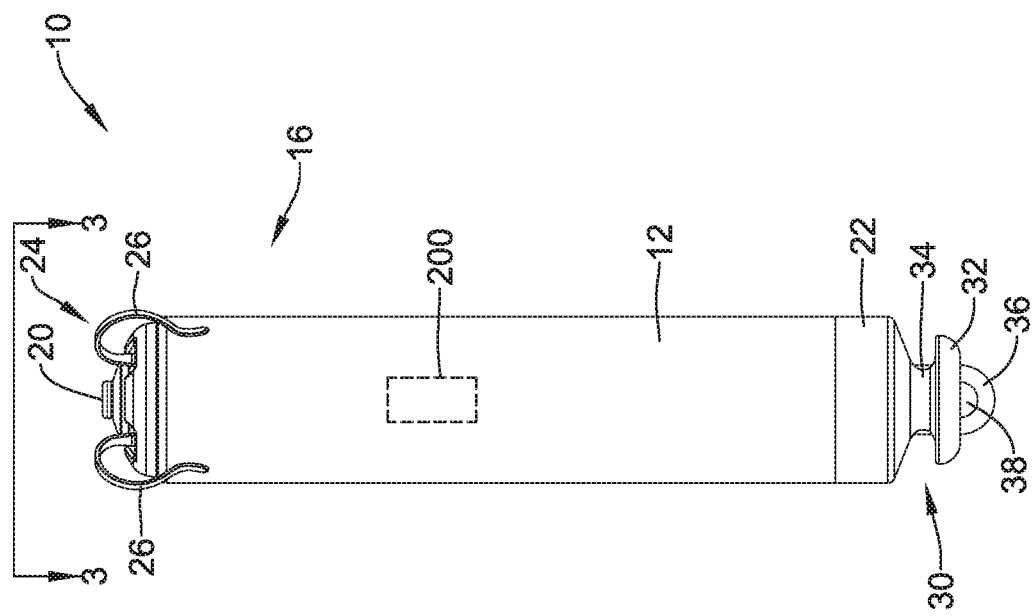
FIG. 2 is a side view of an example implantable leadless cardiac pacing device.
Figure 3:
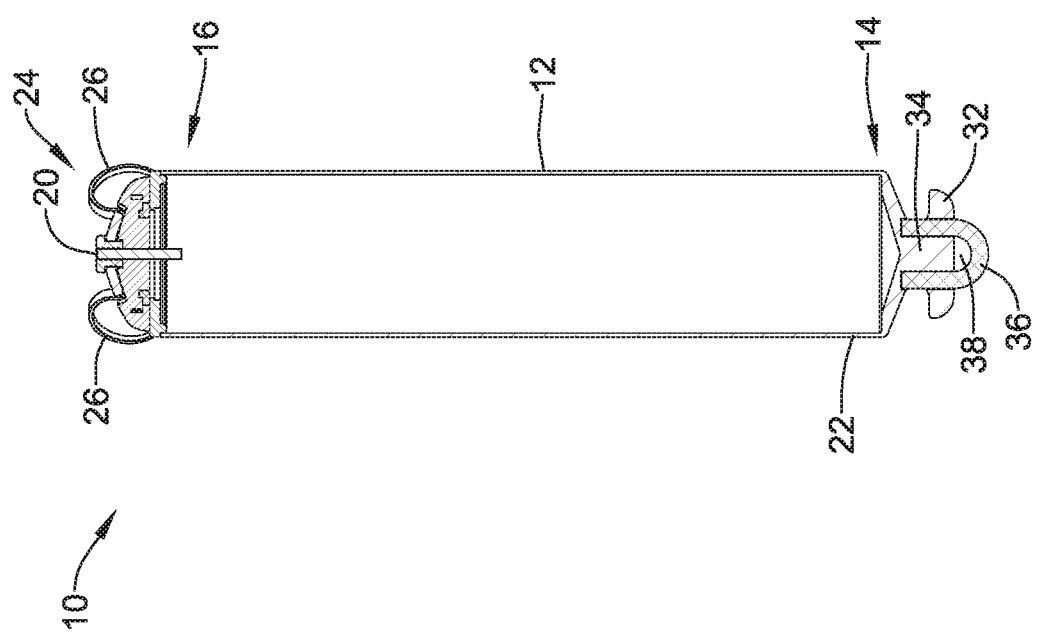
FIG. 3 is a cross-sectional view of the implantable leadless cardiac pacing device of FIG. 2.

FIG. 1 illustrates example implantable leadless cardiac pacing devices 10 (e.g., a leadless pacemaker) implanted in a heart H. An illustrative implantable medical device (IMD) 10 is shown within the right ventricle RV while another IMD 10 is shown within the left ventricle LV as the IMD 10 may be configured for implantation in either ventricle, or in another chamber such as a right atrium RA or a left atrium LA. Depending on therapeutic needs, a patient may have a single IMD 10 or may have two or more IMDs 10 implanted in appropriate chambers. A side view of the illustrative implantable medical device (IMD) 10 is shown in FIG. 2 and a cross-sectional view of the illustrative IMD 10, taken at line 3-3 in FIG. 2, is illustrated in FIG. 3. The implantable medical device 10 may include a shell or housing 12 having a proximal end 14 and a distal end 16. In some instances, the IMD 10 may include a first electrode 20 positioned adjacent to the distal end 16 of the housing 12 and a second electrode 22 positioned adjacent to the proximal end 14 of the housing 12. In some cases, the housing 12 may include a conductive material and may be insulated along at least a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be configured to be positioned against the cardiac tissue of the heart H or may otherwise contact the cardiac tissue of the heart H while the second electrode 22 may be spaced away from the first electrode 20, and thus spaced away from the cardiac tissue.

The IMD 10 may include a pulse generator (e.g., electrical circuitry) and a power source (e.g., a battery) within the housing 12 to provide electrical signals to the electrodes 20, 22 and thus control the pacing/sensing electrodes 20, 22. In some cases, electrical communication between the pulse generator and the electrodes 20, 22 may provide electrical stimulation to heart tissue and/or sense a physiological condition.

The IMD 10 may include a fixation mechanism 24 proximate the distal end 16 of the housing 12 configured to attach the IMD 10 to a tissue wall of the heart H, or otherwise anchor the IMD 10 to the anatomy of the patient. As shown in FIG. 1, in some instances, the fixation mechanism 24 may include one or more, or a plurality of hooks or tines 26 anchored into the cardiac tissue of the heart H to attach the IMD 10 to a tissue wall. In other cases, the fixation mechanism 24 may include one or more, or a plurality of passive tines, configured to entangle with trabeculae within the chamber of the heart H and/or a helical fixation anchor configured to be screwed into a tissue wall to anchor the IMD 10 to the heart H.

The IMD 10 may include a docking member 30 proximate the proximal end 14 of the housing 12 configured to facilitate delivery and/or retrieval of the IMD 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the IMD 10 which is greater than a radial dimension of the neck portion 34 from the longitudinal axis of the IMD 10. The docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g. looped) through the opening 38. The retention structure 36 may extend though the head portion 32, along the neck portion 34, and to or into the proximal end 14 of the housing 12, as is shown more clearly in FIG. 3. The docking member 30 may be configured to facilitate delivery of the IMD 10 to the intracardiac site and/or retrieval of the IMD 10 from the intracardiac site. Other docking members 30 are contemplated.

In some cases, the IMD 10 may include one or more sensors or other devices that facilitate tracking the IMD 10 during and/or after delivery. In some cases, as schematically illustrated, the IMD 10 may include a sensor 200 that is disposed on or within the IMD 10. In some cases, the sensor 200 may be considered to represent one or more magnetic tracking sensors that may facilitate magnetic tracking of the IMD 10 using a system such as will be described with respect to FIG. 20. An illustrative but non-limiting example of such a system is the RHTHYMIA® system available from Boston Scientific. In some cases, the sensor 200 may be considered to represent one or more impedance tracking sensors that may facilitate impedance tracking of the IMD 10. In some cases, the sensor 200 may be considered to represent one or more magnetic tracking sensors and one or more impedance tracking sensors, both of which may facilitate impedance tracking of the IMD 10.

In some cases, the IMD 10 may be delivered to the heart H using a delivery device which may be advanced through a femoral vein, into the inferior vena cava, into the right atrium, through the tricuspid valve, and into the right ventricle. Accordingly, it will be appreciated that the delivery device may need to be navigated through relatively tortuous anatomy to deliver the IMD 10 to a suitable location. The target region for the delivery of the IMD 10 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery system with certain features that may allow for easier or better control for navigation or delivery purposes.

Figure 4:
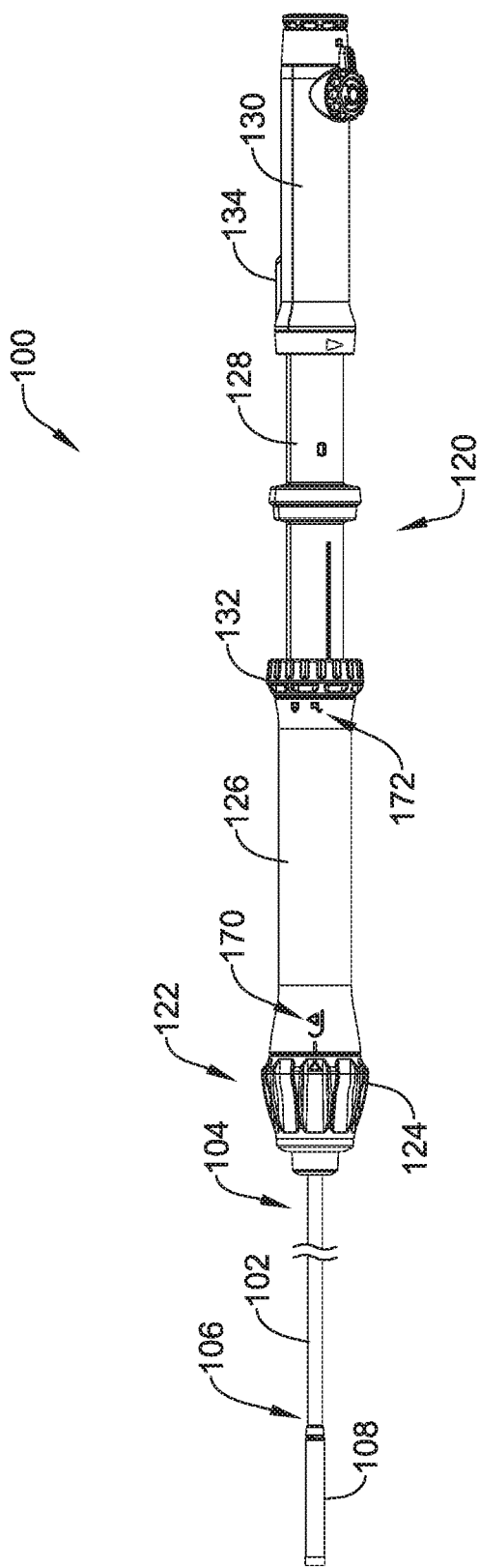
FIG. 4 is a plan view of an example delivery device for an implantable leadless cardiac pacing device.
Figure 5:
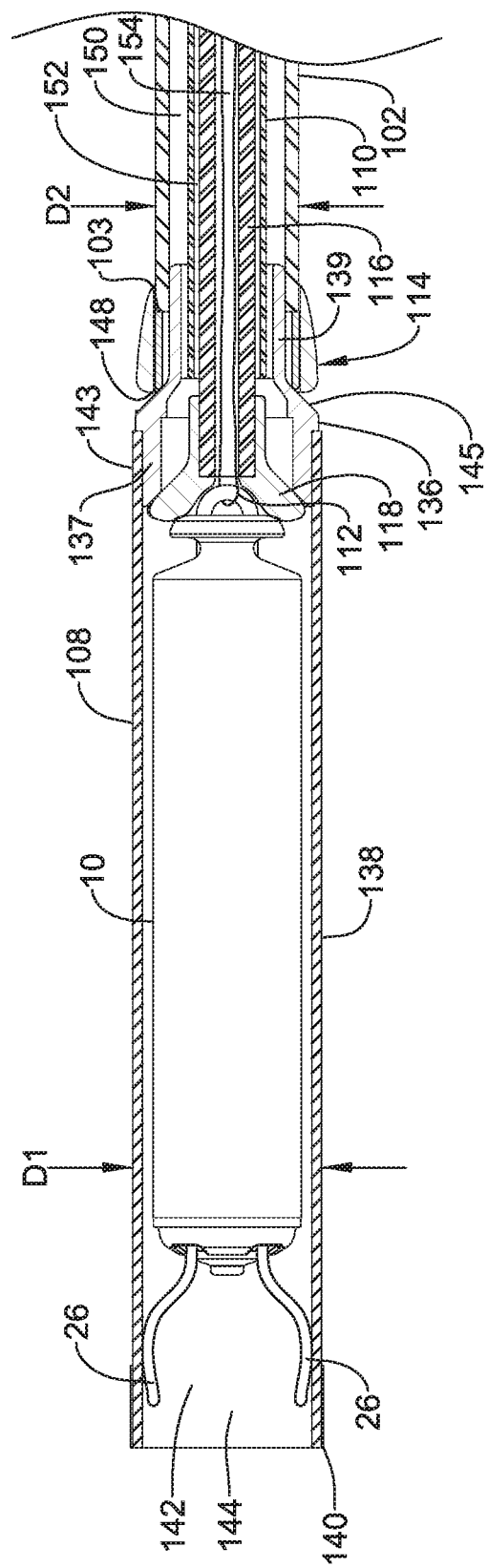
FIG. 5 is a partial cross-sectional side view of the distal portion of the delivery device of FIG. 4.

FIG. 4 is a plan view of an illustrative delivery device 100, such as a catheter, that may be used to deliver the IMD 10. It will be appreciated that the delivery device 100 is merely illustrative, as the IMD 10 may be delivered with other delivery devices that may or may not include some of the features described with respect to the delivery device 100. As illustrated, the delivery device 100 may include an outer tubular member 102 having a proximal section 104 and a distal section 106. An intermediate tubular member 110 may be longitudinally slidably disposed within a lumen 150 of the outer tubular member 102 (see e.g. FIG. 5). An inner tubular member 116 may be longitudinally slidably disposed within a lumen 152 of the intermediate tubular member 110 (see e.g. FIG. 5). A distal holding section, or device containment housing 108 may be attached to a distal end portion 114 of the intermediate tubular member 110, as illustrated in FIG. 5. The delivery device 100 may also include a handle assembly 120 positioned adjacent to the proximal section 104 of the outer tubular member 102. In some instances, the outer tubular member 102 may include at least a section thereof that has an outer diameter D2 that is less than the outer diameter D1 of at least a portion of the device containment housing 108 (see e.g. FIG. 5).

The handle assembly 120 may include a first or distal hub portion 126 attached to, such as fixedly attached to, the proximal end section 104 of the outer tubular member 102, a second or intermediate hub portion 128 attached to, such as fixedly attached to, a proximal end section of the intermediate tubular member 110, and a third or proximal hub portion 130 attached to, such as fixedly attached to, a proximal end section of the inner tubular member 116 (see e.g. FIG. 5). The first hub portion 126, second hub portion 128, and third hub portion 130 may be positioned in a generally telescoping arrangement and longitudinally slidable relative to each other. As will be discussed in more detail below, each of the first hub portion 126, the second hub portion 128, and the third hub portion 130 may be longitudinally slidable and rotatable relative to each other such that the outer tubular member 102, intermediate tubular member 110, and inner tubular member 116 may be individually actuated. In some instances, it may be desirable to move the outer tubular member 102, intermediate tubular member 110 and inner tubular member 116 simultaneously. The handle assembly 120 may include a multi-stage deployment mechanism or a first locking mechanism 134 to releasably couple the second hub portion 128 to the third hub portion 130 to prevent relative longitudinal movement therebetween, and thus prevent relative longitudinal movement between the intermediate tubular member 110 and the inner tubular member 116, as will be discussed in more detail below. The handle assembly 120 may also include a second locking mechanism 132 to releasably couple the first hub portion 126 to the second hub portion 128 to prevent relative longitudinal movement therebetween, and thus prevent relative longitudinal movement between the outer tubular member 102 and the intermediate tubular member 110, as will be discussed in more detail below.

The device containment housing 108 may be configured to receive the IMD 10 therein. For example, referring to FIG. 5, which illustrates a cross-sectional view of a distal portion of the delivery device 100, the device containment housing 108 may define a cavity 142 for slidably receiving the IMD 10, and may include a distal opening 144 for slidable insertion and/or extraction of the IMD 10 into and/or out of the cavity 142. The device containment housing 108 may include a body portion 138 and a distal tip portion 140 that may be, for example, configured to be atraumatic to anatomy, such as a bumper tip. For example, as the catheter is navigated through the anatomy, the distal tip may come into contact with anatomy. Additionally, when the catheter is used to deliver the implantable medical device 10, the tip 140 of the delivery device 100 will likely come into contact with tissue adjacent the target site (e.g. cardiac tissue of the heart).

In some cases, a hard distal tip formed of the material of the outer tubular member 102 and/or intermediate tubular member 110 may injure a vessel wall or cardiac tissue. As such, it may be desirable to provide the delivery device 100 with a softer distal tip 140 that can be introduced into the anatomy and come into contact with anatomy adjacent the target cite without causing unnecessary trauma. In some cases, the distal tip 140 may be made of a material that is softer than the body portion 138 of the device containment housing 108. In some cases, the distal tip 140 may include a material that has a durometer that is less than the durometer of the material of the body portion 138. In some particular embodiments, the durometer of the material used in the distal tip 140 may be in the range of about 5 D to about 70 D, or for example, in the range of about 25 D to about 65 D. Additionally, the distal tip 140 may include a shape or structure that may make it less traumatic to tissue. For example, the distal tip 140 may have a distal surface, such as a tissue contacting surface, that is that is rounded or includes a curvature configured to be more atraumatic to tissue.

In some instances, all or a portion of the device containment housing 108 may include an inner surface that may be configured to resist getting caught on the fixation mechanism 24, such as the one or more, or a plurality of hooks or tines 26 on the implantable medical device 10. For example, the device containment housing 108 may include an inner layer or coating of harder or more lubricious material that resists force applied by the fixation mechanism 24 onto the inner surface of the device containment housing 108. For example, the device containment housing 108 may include a multi-layered structure, and an inner layer may be made of a material that is harder than an outer layer.

The inner tubular member 116 may be disposed (e.g., slidably disposed) within a lumen 152 of the intermediate tubular member 110. The inner tubular member 116 may be engaged by a user near or at the third hub portion 130, and extend through a lumen 152 of the intermediate tubular member 110 and into the device containment housing 108. A distal portion 118 of the inner tubular member 116 may be capable of engaging the IMD 10, and the inner tubular member 116 may be used to "push" the IMD 10 out from device containment housing 108 so as to deploy and anchor the IMD 10 within a target region (e.g., a region of the heart such as the right ventricle). The inner tubular member 116 may have a lumen 154 extending from the proximal end 117 to a distal portion 118 thereof. A tether 112 or other retaining feature may be used to releasably secure the IMD 10 to the delivery device 100. In some instances, the tether 112 may be a single or unitary length of material that may extend from a proximal end 117 of the lumen 154, out through the distal portion 118, through the opening 38 of the IMD 10 and return to the proximal end 117 of the inner tubular member 116 through the lumen 154 such that both ends of the tether 112 are positioned adjacent to the third hub portion 130. In some instances, as will be discussed in more detail below, the ends of the tether 112 may be secured within a locking feature in the third hub portion 130.

In order to more specifically place or steer the delivery device 100 to a position adjacent to the intended target, the delivery device 100 may be configured to be deflectable or articulable or steerable. Referring to FIG. 4, for example, the outer tubular member 102 and/or intermediate tubular member 110 may include one or more articulation or deflection mechanism(s) that may allow for the delivery device 100, or portions thereof, to be deflected, articulated, steered and/or controlled in a desired manner. For example, the outer tubular member 102 may include at least a portion thereof that can be selectively bent and/or deflected in a desired or predetermined direction. This may, for example, allow a user to orient the delivery device 100 such that the device containment housing 108 is in a desirable position or orientation for navigation or delivery of the IMD 10 to a target location. The outer tubular member 102 may be deflected, for example, along a deflection region.

A wide variety of deflection mechanisms may be used. In some example embodiments, deflection may be effected by one or more actuation members, such as pull wire(s) extending between a distal portion of the outer tubular member 102 and an actuation mechanism 122 near the proximal end of the outer tubular member 102. As such, the one or more pull wires may extend both proximally and distally of the desired deflection or bending region or point. This allows a user to actuate (e.g., "pull") one or more of the pull wires to apply a compression and/or deflection force to at least a portion of the outer tubular member 102 and thereby deflect or bend the outer tubular member 102 in a desired manner. In addition, in some cases the one or more wires may be stiff enough so that they can also be used to provide a pushing and/or tensioning force on the outer tubular member 102, for example, to "push" or "straighten" the shaft into a desired position or orientation.

In some embodiments, the actuation member takes the form of a continuous wire that is looped through or otherwise coupled to a distal end region of the outer tubular member 102 so as to define a pair of wire sections. Other embodiments are contemplated, however, including embodiments where the actuation member includes one or a plurality of individual wires that are attached, for example, to a metal or metal alloy ring adjacent the distal end region of the outer tubular member 102.

The actuation mechanism 122 may include a desired mechanism that may allow for applying tension (i.e. pulling force), or compression (i.e. pushing force), or both, on the actuation member(s). In some embodiments, the actuation mechanism 122 may include an external rotatable member 124 connected to and rotatable about the longitudinal axis of the handle assembly 120. The rotatable member 124 may threadingly engage an internal member that is attached to the proximal end of the actuation member(s) or pull wires. When the external rotatable member 124 is rotated in a first rotational direction, the internal member translates in a first longitudinal direction, thereby applying tension to the pull wire(s), which applies compression force to the shaft, so as to deflect the outer tubular member 102 from an initial position to a deflected position. When the external rotatable member 124 is rotated in a second rotational direction, the internal member translates in a second longitudinal direction, thereby reducing and/or releasing the tension on the pull wire(s), and allowing the outer tubular member 102 to relax back toward the initial position. Additionally, in some cases, as mentioned above, where the one or more wires may be stiff enough, rotation of the rotatable member 124 in the second rotational direction such that the internal member translates in a second longitudinal direction may apply compression to the wire(s), such that the wire(s) may apply tension to the outer tubular member 102 and "push" the outer tubular member 102 back toward an initial position, and possibly into additional positions beyond the initial position.

The one or more articulation and/or deflection mechanism(s) may also entail the outer tubular member 102 including structure and/or material that may provide for the desired degree and/or location of the deflection when the compressive or tensile forces are applied. For example, the outer tubular member 102 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the outer tubular member 102.

In other embodiments, other articulation and/or deflection mechanism(s) are contemplated. For example, all or a portion of the delivery device 100, such as the outer tubular member 102, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material and mechanism may be used to deflect or bend the outer tubular member 102 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the outer tubular member 102 may include one or more predefined or fixed curved portion(s) along the length thereof. In some cases, such curved sections may be configured to fit with particular anatomies or be configured for better navigation or delivery of the IMD 10. Additionally, or alternatively, some such curved sections may be configured to allow the outer tubular member 102 to be predisposed to be bent and/or deflected in a certain direction or configuration when compression and/or tension forces are applied thereto. In some cases, the outer tubular member 102 may be a laser cut metallic tubing, a braid reinforced polymeric tubing, or other flexible tubular structure as desired.

Returning again to FIG. 5, the device containment housing 108 may be affixed to a distal end portion 114 of the intermediate tubular member 110. The device containment housing 108 may include a hub portion 136 and a tubular body portion 138. In some instances, the hub portion 136 may be formed from a metal or metal alloy while the body portion 138 may be formed from a polymeric material, although this is not required. In some instances, a proximal region 143 of the body portion 138 may be heat bonded to a distal end portion 137 of the hub portion 136, or otherwise affixed. The hub portion 136 may include a tapered intermediate region 145 disposed between a proximal end portion 139 and the distal end portion 137.

In some cases, the outer tubular member 102 may include a metal ring or tip adjacent the distal end 103 thereof for attaching one or more pull wires thereto. In some cases, the outer tubular member 102 may further include a lubricious liner, such as, but not limited to a polytetrafluoroethylene (PTFE) liner. The proximal end portion 139 of the hub portion 136 may extend proximally into the lumen 150 of the outer tubular member 102. In some instances, an outer surface of the proximal end portion 139 may form an interference fit with an inner surface of the outer tubular member 102. In some cases, the outer surface of the proximal end portion 139 and the inner surface of the outer tubular member 102 may be coupled in a tapered engagement. For example, the distal end 103 of the outer tubular member 102 may flare radially outwards in the distal direction and/or the proximal end portion 139 may taper radially inward in the proximal direction. The two angled surfaces may engage as the proximal end portion 139 is proximally retracted within the outer tubular member 102. Other coupling arrangements may be used as desired.

In some cases, as the outer tubular member 102 is bent to navigate the IMD 10 to the desired location, the proximal end portion 139 may advance distally and disengage from the inner surface of the outer tubular member 102 creating a kink point or weakened region adjacent to the bonding region 146. Proximally retracting the intermediate tubular member 110 to bring the intermediate region 145 into contact with the outer tubular member 102 at contact point 148 and/or bringing the proximal end portion 139 into the outer tubular member 102 and fixing the intermediate tubular member 110 in this configuration may help prevent migration of the device containment housing 108 during navigation of the delivery device 100 to the desired location. Such a configuration may also place the intermediate tubular member 110 in tension while the device containment housing 108 applies a compression force on the outer tubular member 102, as will be discussed in more detail below. As discussed above, a locking mechanism 132 in the handle assembly 120 may be utilized to releasably maintain the outer tubular member 102 and the intermediate tubular member 110 in a desired orientation.

Figure 6:
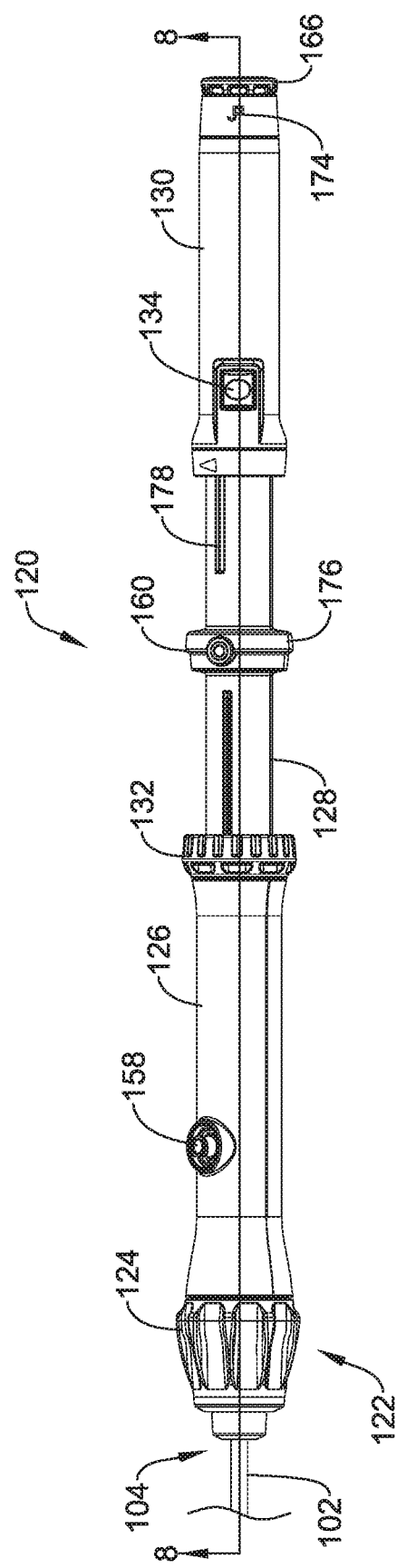
FIG. 6 is a top view of the handle of the illustrative delivery device of FIG. 4.
Figure 7:
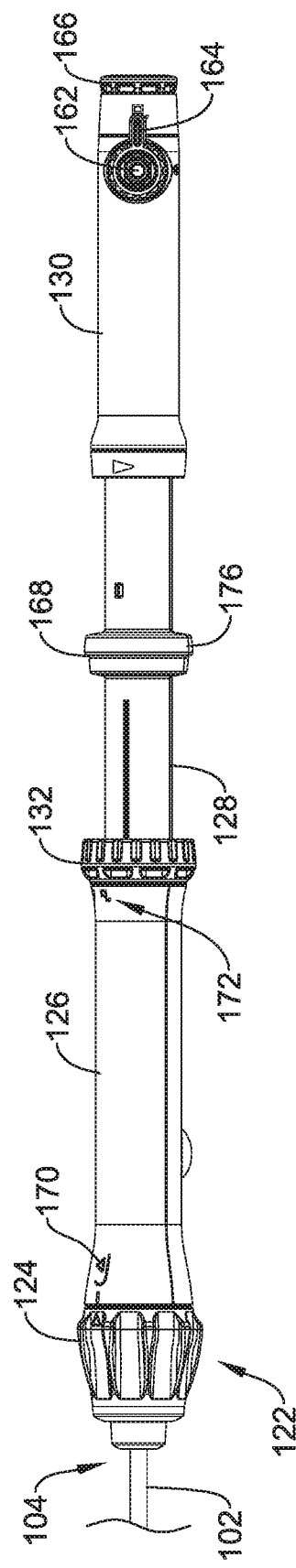
FIG. 7 is a bottom view of the handle of the illustrative delivery device of FIG. 4.

FIG. 6 illustrates a top view of the handle assembly 120 of the delivery device 100. FIG. 7 illustrates a bottom view of the handle assembly, approximately 180° from the view shown in FIG. 6. The handle assembly 120 may include one or more ports 158, 160, 162 for delivering fluids, such as, but not limited to, a contrast and/or flushing fluid to the cavity 142 of the device containment housing 108. The flush ports 158, 160, 162 may be in fluid communication with the lumens 150, 152, 154 of the outer, intermediate or inner tubular members 102, 110, 116, as desired. For example, the flush port 158 may be in fluid communication with the lumen 150 of the outer tubular member 102, the flush port 160 may be in fluid communication with the lumen 152 of the intermediate tubular member 110, and the flush port 162 may be in fluid communication with the lumen 154 of the inner tubular member 116.

The handle assembly 120 may further include a tether lock 164. The tether lock 164 may be actuatable between a locked and an unlocked configuration to maintain the tether 112 in a desired orientation. The ends of the tether 112 may affixed to, secured to, or otherwise engage a tether cap 166 positioned at a proximal end of the third hub portion 130. The tether cap 166 may be removably secured to the third hub portion 130 to allow a clinician access to the ends of the tether 112. When the tether lock 164 is in the locked configuration, the tether cap 166 may not be removed from the third hub portion 130. When the tether lock 164 is in the unlocked configuration, the tether cap 166 may be removed and the ends of the tether 112 may be actuated. For example, once the IMD 10 has been implanted and its location verified, the tether 112 may be removed from the tether retention feature 36 of the IMD 10 by pulling on one of the ends until the opposite end has passed through the opening 38 such that the IMD 10 is free from the tether 112.

In some instances, the handle assembly 120 may also include visual markings, such as, but not limited to the markings illustrated at 170, 172, 174. These markings 170, 172, 174 may provide visual instructions or indications to the clinician. For example, the marking shown at 170 may be positioned proximate the rotatable member 124 of the actuation mechanism 122 to indicate that the rotatable member 124 controls deflection of the outer tubular member 102 and/or to indicate which direction the distal section 106 will deflect when the rotatable member 124 of the actuation mechanism 122 is rotated in a given direction. The markings shown at 172 may provide an indication of whether the second locking mechanism 132 is in the unlocked and/or locked configuration. Similarly, the markings shown at 174 may provide an indication of whether the tether lock 164 is in the unlocked and/or locked configuration.

Figure 8:
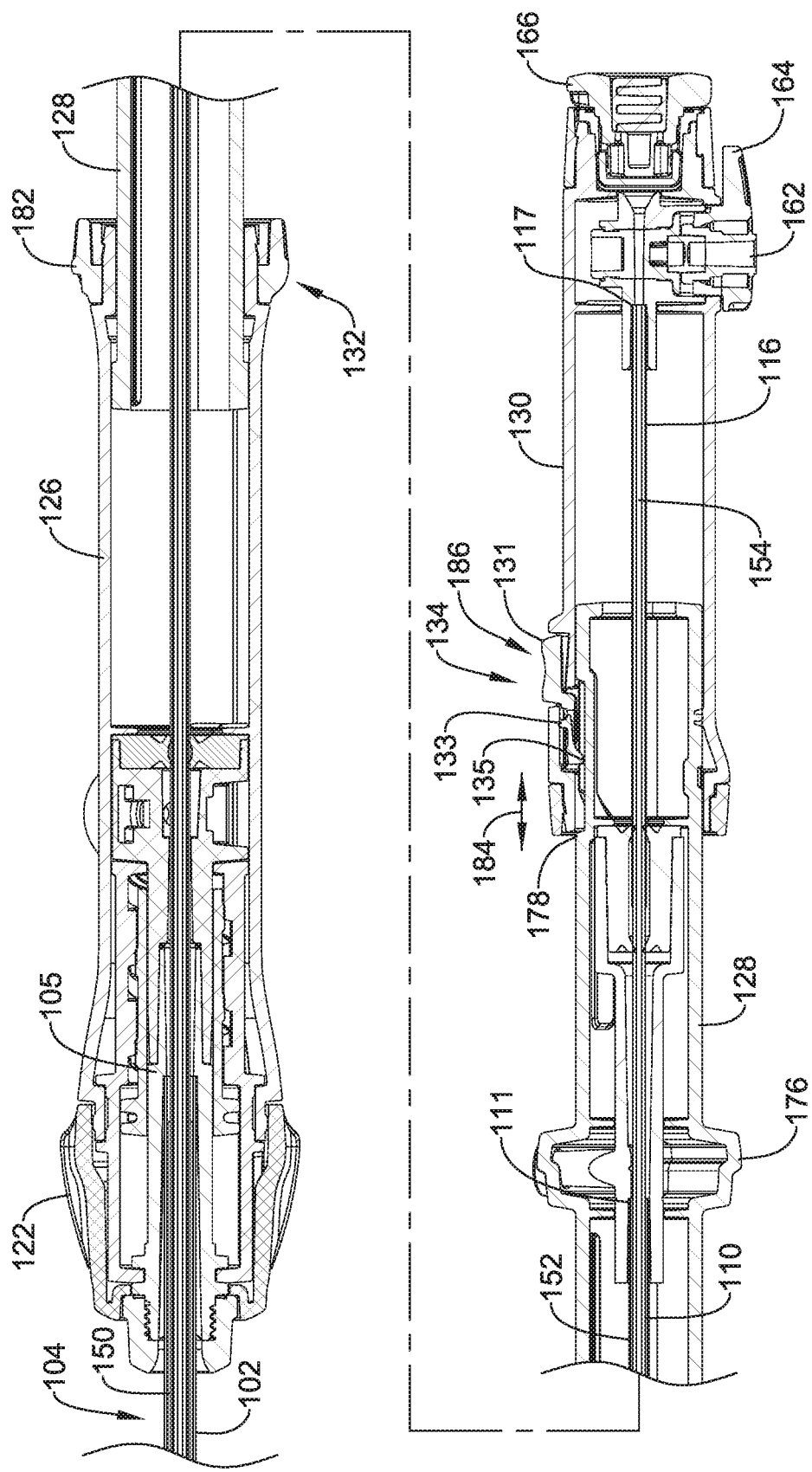
FIG. 8 is a cross-section view of the handle of the illustrative delivery device of FIG. 4 taken at line 8-8 in FIG. 6.

FIG. 8 illustrates a cross-sectional view of the handle assembly 120 of the delivery device. As discussed above, the handle assembly 120 may include a first hub portion 126 attached to the proximal end section 104 of the outer tubular member 102, a second hub portion 128 attached to a proximal end section of the intermediate tubular member 110, and a third hub portion 130 attached to a proximal end section of the inner tubular member 116. Each of the first hub portion 126, the second hub portion 128, and the third hub portion 130 may be slidable and rotatable relative to each other such that the outer tubular member 102, intermediate tubular member 110, and inner tubular member 116 may be individually longitudinally actuated.

The inner tubular member 116 may extend distally from a proximal end 117. The proximal end 117 of the inner tubular member 116 may be positioned within or adjacent to the tether lock 164. The tether lock 164 may include a port 162 which may be in fluid communication with a lumen 154 of the inner tubular member 116. The lumen 154 may extend from the proximal end 117 to the distal portion 118 for delivering fluids, such as, but not limited to, a contrast and/or flushing fluid to the cavity 142 of the device containment housing 108. In some instances, the inner tubular member 116 may be coupled or affixed to the third hub portion 130 adjacent the proximal end 117 of the inner tubular member 116, although this is not required. In some cases, the inner tubular member 116 may be affixed to the third hub portion 130 at any longitudinal location desired. In some instances, a tether, such as tether 112, for securing the IMD 10 to the distal portion 118 of the inner tubular member 116 may be disposed within the lumen 154 and may exit the delivery device 100 through or adjacent to tether cap 166, although this is not required.

The intermediate tubular member 110 may extend distally from a proximal end 111. The proximal end 111 of the intermediate tubular member 110 may be positioned within the second hub portion 128. The intermediate tubular member 110 may include a lumen 152 extending from the proximal end 111 to a distal end of the intermediate tubular member 110. The inner tubular member 116 may be slidably disposed within the lumen 152 of the intermediate tubular member 110. In some instances, the intermediate tubular member 110 may be coupled or affixed to the second hub portion 128 adjacent the proximal end 111 of the intermediate tubular member 110, although this is not required. In some cases, the intermediate tubular member 110 may be affixed to the second hub portion 128 at any longitudinal location desired.

The outer tubular member 102 may extend distally from a proximal end 105. The proximal end 105 of the outer tubular member 102 may be positioned within the first hub portion 126. The outer tubular member 102 may include a lumen 150 extending from the proximal end 105 to a distal end 103 of the outer tubular member 102. The intermediate tubular member 110 may be longitudinally slidably disposed within the lumen 150 of the outer tubular member 102. In some instances, the outer tubular member 102 may be coupled or affixed to the first hub portion 126 adjacent the proximal end 105 of the outer tubular member 102, although this is not required. In some cases, the outer tubular member 102 may be affixed to the first hub portion 126 at any longitudinal location desired.

In some instances, the first hub portion 126 may include a retaining ring 182 positioned adjacent to a proximal end of the first hub portion 126. In some instances, the retaining ring 182 may be rotatable about a longitudinal axis of the handle assembly 120. In some cases, the retaining ring 182 may include locking features configured to engage with other locking features of the locking mechanism 132. When the retaining ring 182 engages other features of the locking mechanism 132, longitudinal movement of the first hub portion 126 and the second hub portion 128 relative to one another may be prevented. Rotating the retaining ring 182 may disengage the retaining ring 182 from the other features of the locking mechanism 132. This may allow for longitudinal movement of the first hub portion 126 and the second hub portion 128 relative to one another, as will be described in more detail below. While the second locking mechanism 132 is described as a rotating retaining ring 182, other locking mechanisms capable of releasably securing first hub portion 126 and the second hub portion 128, and thus the outer tubular member 102 and the intermediate tubular member 110, may be used.

In some instances, the first locking mechanism 134 may include a depressible button 131. The depressible button 131 may include a first outwardly protruding portion 133 configured to engage a region of the third hub portion 130 and a second inwardly protruding portion 135 configured to engage a region of the second hub portion 128. For example, the second protruding portion 135 may be disposed in and engage a groove or recess 178 formed in the second hub portion 128. The engagement of the first locking mechanism 134 may prevent or reduce relative movement of the second hub portion 128 and the third hub portion 130 when the first locking mechanism 134 is not actively actuated (e.g. depressed) by a clinician. A downward force 186 may be applied to the button 131. The force 186 may cause the first protruding portion 133 to lower and/or disengage from a surface of the third hub portion 130 and the second protruding portion 135 to raise and/or disengage from a surface of the second hub portion 128. This may allow the third hub portion 130 to be moved longitudinally (e.g., proximally and/or distally), as shown at 184, along a longitudinal axis of the handle assembly 120 relative to the second hub portion 128, as will be discussed in more detail below. Longitudinal actuation of the third hub portion 130 relative to the second hub portion 128 may result in a corresponding longitudinal actuation of the inner tubular member (and hence the IMD 10) relative to the intermediate tubular member 110 and the device containment housing 108. Such actuation may be used to incrementally deploy the IMD 10. FIG. 8 illustrates the second protruding portion 135 disposed in the middle of the recess 178. However, in some cases, during advancement of the delivery device 100 to the desired treatment location, the second protruding portion 135 may be positioned at the proximal end of the recess 178 to ensure the IMD 10 is fully disposed in the device containment housing 108. This is just an example. While the first locking mechanism 134 is described as a depressible button 131, in some cases other locking mechanisms capable of releasably securing the second hub portion 128 and the third hub portion 130, and thus the intermediate tubular member 110 and the inner tubular member 116, may be used.

Figure 9:
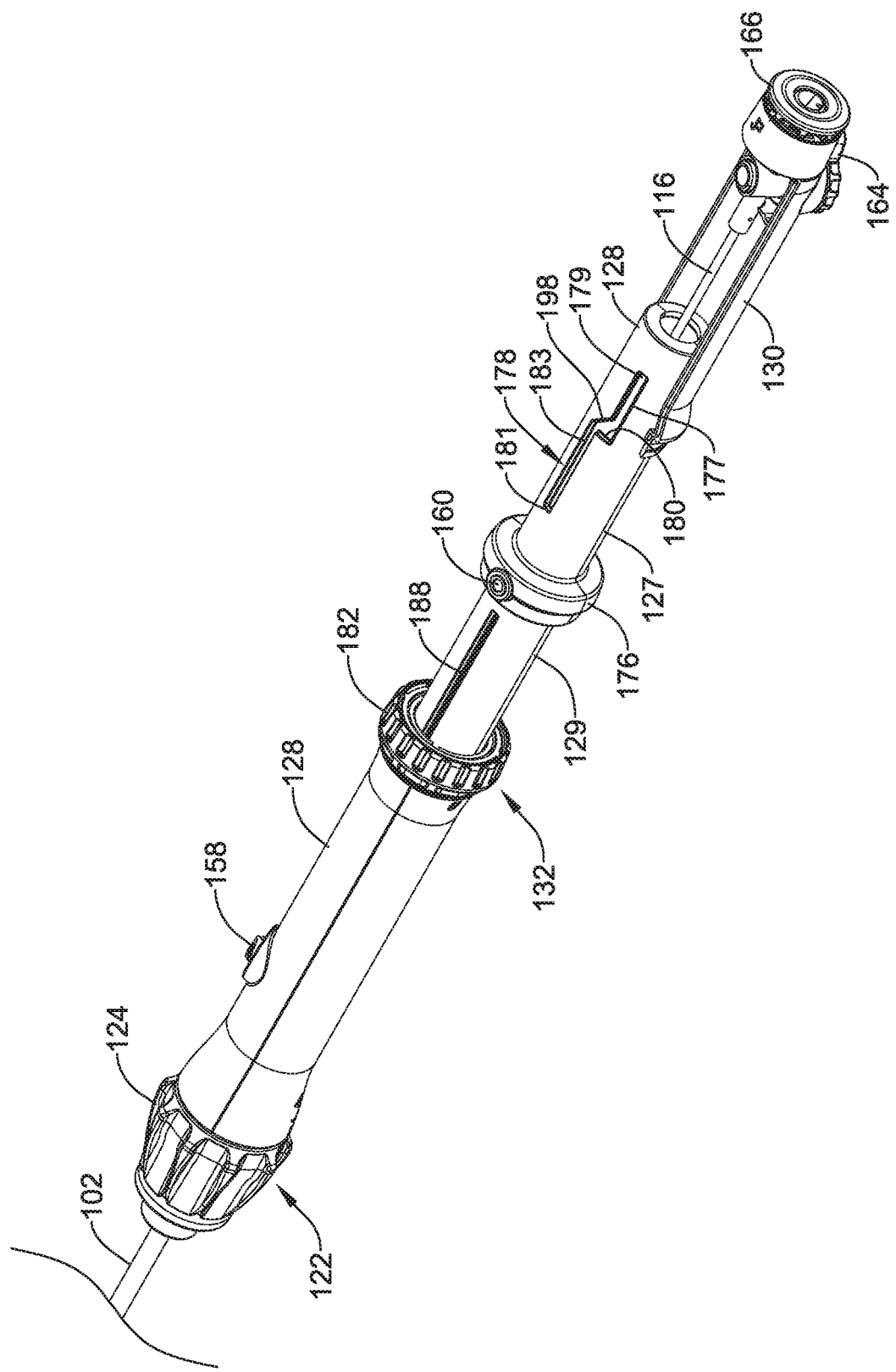
FIG. 9 is a perspective view of the handle of the illustrative delivery device of FIG. 4 with portions removed.

FIG. 9 illustrates a partial perspective view of the handle assembly 120 with portions of the third hub portion 130 removed to more clearly illustrate features of the second hub portion 128. A proximal portion 127 of the second hub portion 128 may include a groove or recess 178 formed therein. The groove 178 may extend from a proximal end 179 to a distal end 181. In some embodiments, groove 178 may include a proximal portion 177 and a distal portion 183 which may be circumferentially offset from one another. A hard stop 180 may be provided at a region between the proximal end 179 and the distal end 181. The hard stop 180 may be a wall or other protrusion configured to engage the second protruding portion 135 of the first locking mechanism 134 such that in order to advance the second protruding portion 135 distally past the hard stop 180 from the proximal portion 177, the user rotates the third hub portion 130 to align the second protruding portion 135 with the distal portion 183 of the groove 178. This may allow the implantable medical device 10 to be incrementally deployed. During advancement of the delivery device 100 through the vasculature, the second protruding portion 135 may be disposed within the proximal portion 177 adjacent to the proximal end 179. As discussed above, the second protruding portion 135 may engage a surface of the second hub portion 128 to prevent and/or minimize relative movement of the second and third hub portions 128, 130 relative to one another.

The groove 178 may also include an angled region 198 between the proximal portion 177 and the distal portion 183 positioned generally opposite the hard stop 180. When the third hub portion 130 is proximally retracted from the distal end 181 to the proximal end 179, the angled region 198 may guide the second protruding portion 135 from the distal portion 183 of the groove 178 to the proximal portion 177 of the groove in a single fluid movement. For example, the third hub portion 130 may be proximally retracted from the distal end 181 to the proximal end 179 relative to the second hub portion 128 in a single proximal movement, if so desired, without prohibiting travel of the second protruding portion 135 from the distal portion 183 to the proximal portion 177.

A distal portion 129 of the second hub portion 128 may include a groove or recess 188 configured to receive a mating feature disposed on the first hub portion 126. This may allow the first hub portion 126 to be proximally retracted over the second hub portion 128, as will be discussed in more detail below. The proximal and distal portions 127, 129 of the second hub portion 128 may be separated by a gripping region 176 configured to provide a region for the clinician to hold.

Figure 10A:
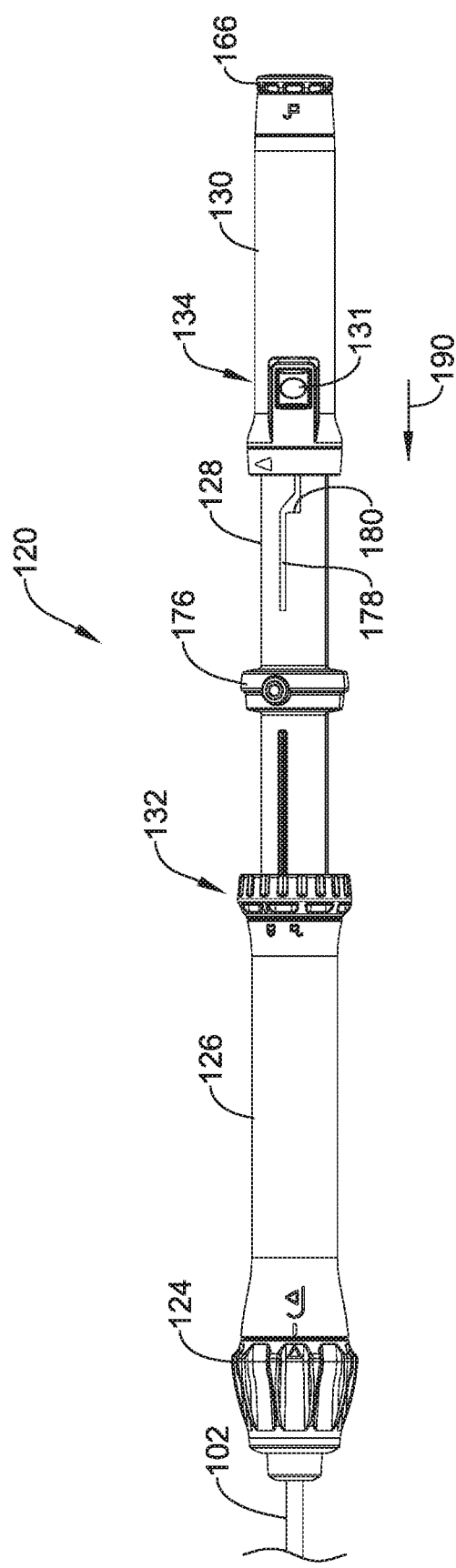
FIGS. 10A-10E are schematic views illustrating the use of the illustrative delivery device to deploy an implantable leadless cardiac pacing device.
Figure 10B:
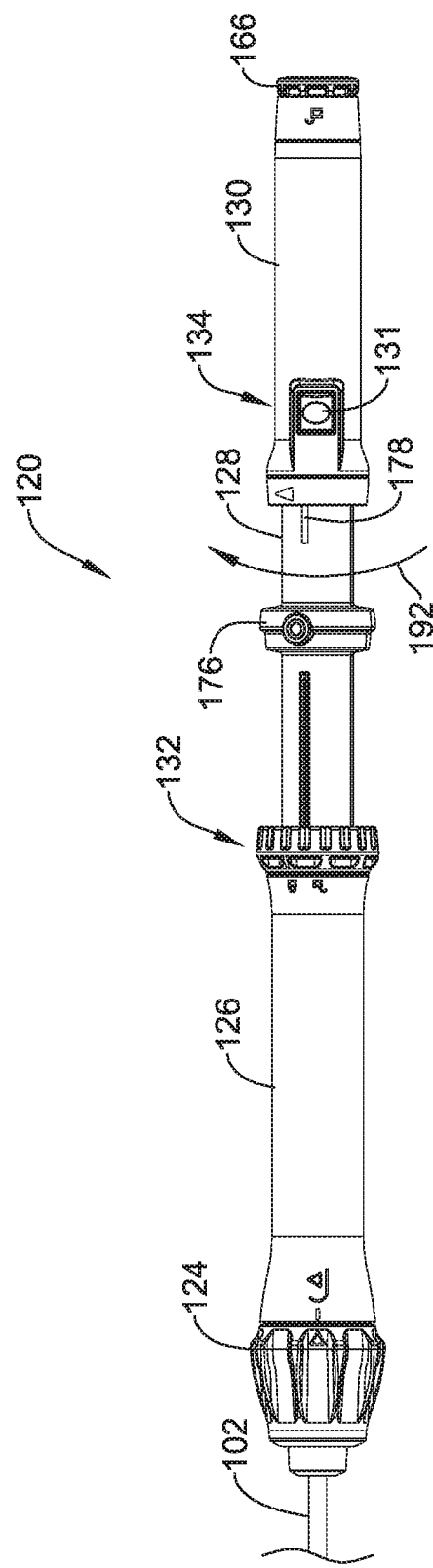

Referring now to FIGS. 10A-10E, a method for deploying an IMD 10 using the illustrative delivery device 100 will now be described. For simplicity, these Figures show the IMDS 10 being delivered to the right ventricle RV. The delivery device 100 may be introduced into the vasculature through the femoral vein through a previously introduced guide catheter. This is just an example. It will be appreciated that the IMD 10 may be delivered and deployed in the left ventricle LV via an intra-aortic approach through the left atrium LA, for example. The delivery device 100 may be introduced through any desired location and with or without the use of a guide catheter as desired. The delivery device 100 may be advanced through the vasculature to the desired treatment location, which, in the case of a leadless cardiac pacing device, may be a chamber of the heart. The clinician may use the actuation mechanism 122 may to deflect the distal section 106 of the outer tubular member 102 in a desired manner to facilitate advancement of the delivery device 100. During advancement of the delivery device 100, the handle assembly 120 may be in a fully extended configuration, as shown in FIG. 10A. In such a configuration, the third hub portion 130 may be at its proximal-most location relative to the second hub portion 128 and the first hub portion 126 may be at its distal-most location relative to the second hub portion 128. When the handle assembly 120 is in its fully extending configuration, the inner tubular member 116, intermediate tubular member 110, and the outer tubular member 102 may be oriented in the manner illustrated in FIG. 5. The delivery device 100 can be imaged using known techniques to ensure accurate placement of the IMD 10.

Figure 10C:
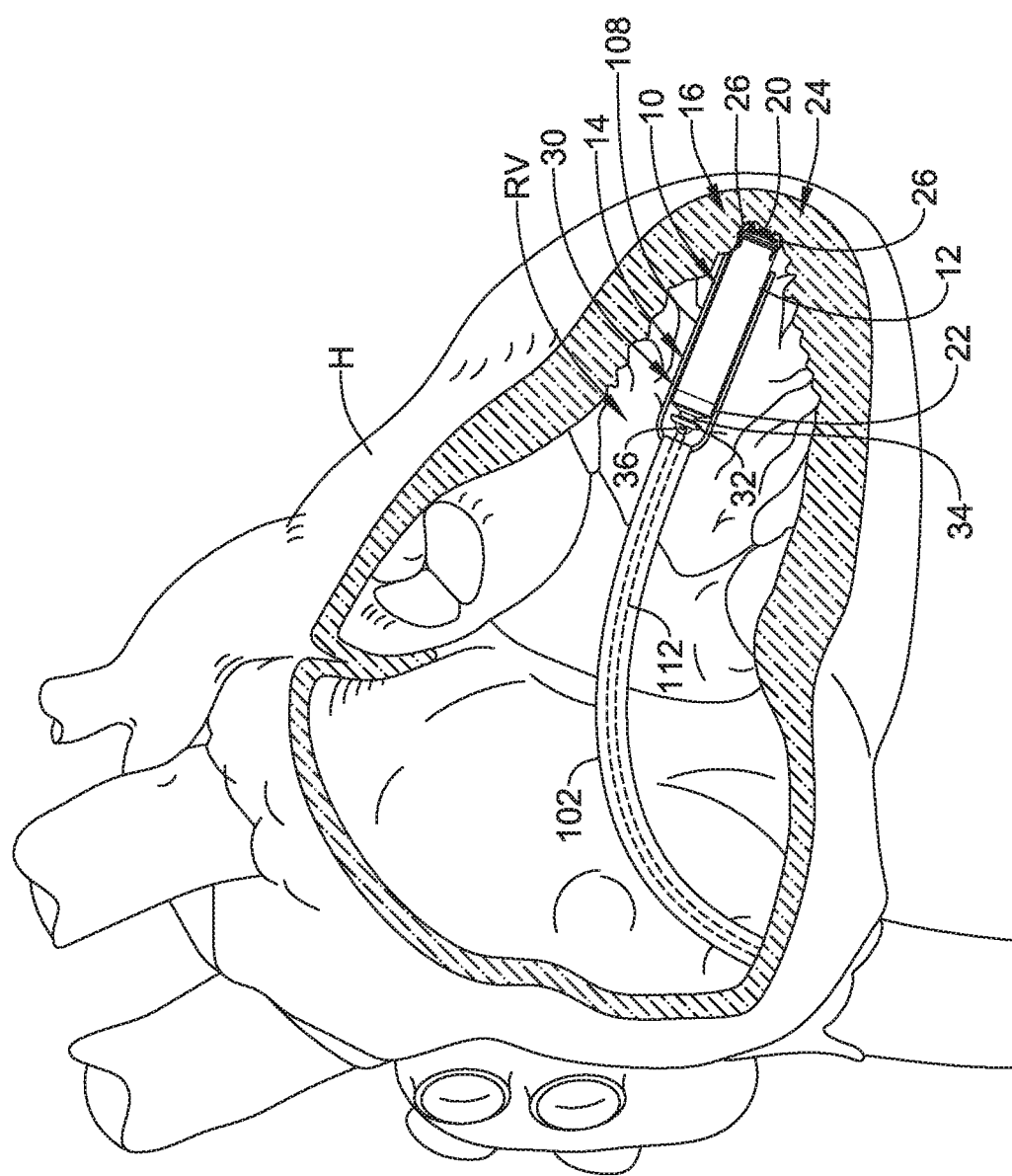
Figure 10D:
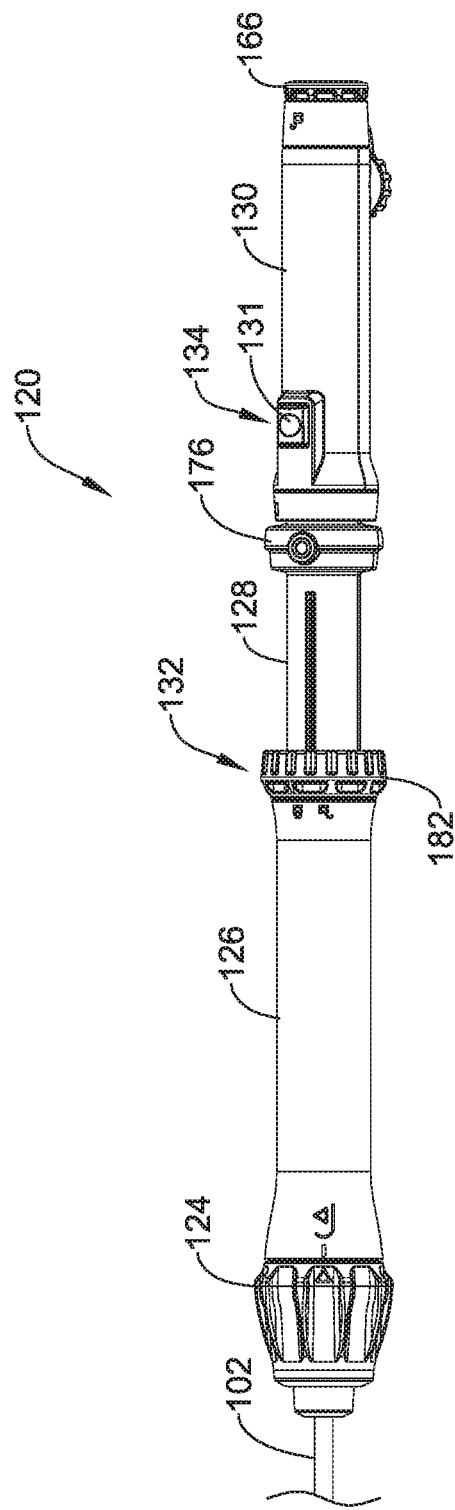

Once the distal tip portion 140 of the device containment housing 108 has been positioned adjacent to the cardiac tissue where the IMD 10 is desired, deployment of the IMD 10 can begin. The first stage of deploying the IMD 10 may enable activation of the fixation mechanism 24. To initiate the first stage of deployment, the clinician may stabilize the first hub portion 126 relative to the patient and depress the button 131 of the first locking mechanism 134. The clinician may then slide the third hub portion 130 distally, as shown at 190, until the first locking mechanism 134 engages the hard stop 180 provided in the second hub portion 128 resulting in the handle assembly 120 configuration shown in FIG. 10B. Distal actuation of the third hub portion 130 may also move the inner tubular member 116 distally by the same distance. As the inner tubular member 116 advances distally, the distal portion 118 may "push" against the proximal end 14 of the implantable medical device 10. As the IMD 10 is pushed distally, the hooks 26 engage the heart tissue as shown in FIG. 10C. The IMD 10 may be distally advanced out of the device containment housing 108 to deploy the hooks or tines 26 from the device containment housing 108 to engage the hooks or tines 26 in the heart tissue while the proximal portion of the IMD 10 remains within the device containment housing 108. In some instances, the IMD 10 may be advanced distally in the range of 1 to 5 millimeters, although this is merely illustrative. This may allow the IMD 10 to be deployed while minimizing the amount of pressure applied to the heart wall. Further, the first locking mechanism 134 may prevent accidental or unintentional deployment of the IMD 10 as the button 131 must be actuated while advancing the third hub portion 130.

Figure 11A:
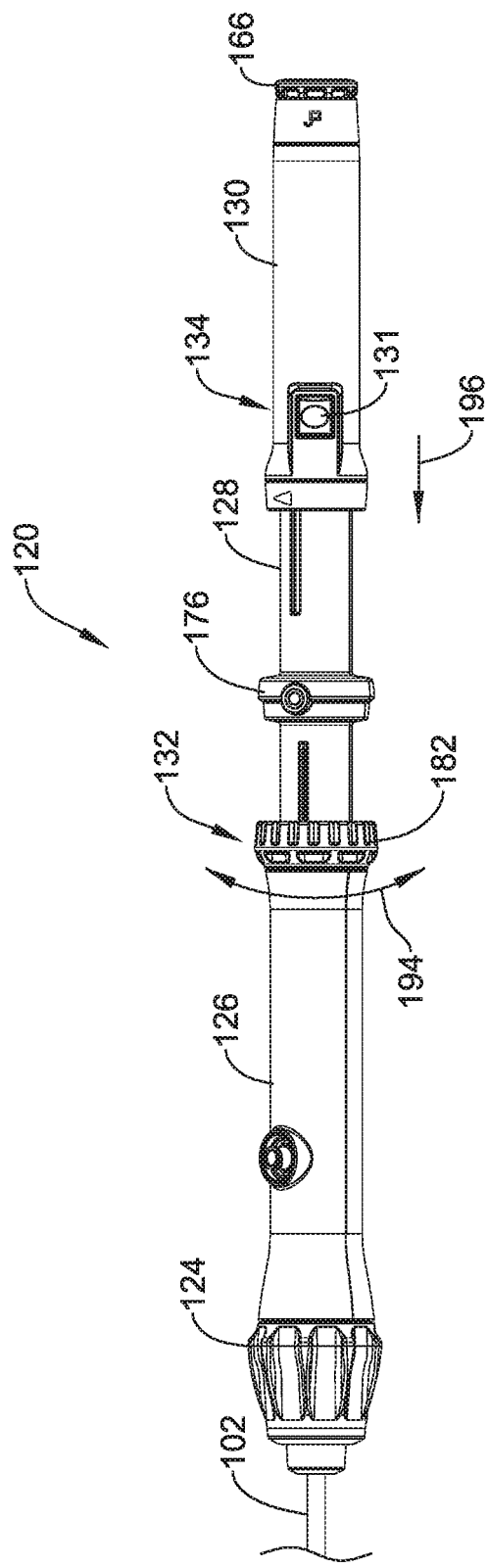
FIGS. 11A-11B are schematic views illustrating an example telescoping feature of the illustrative delivery device.
Figure 11B:
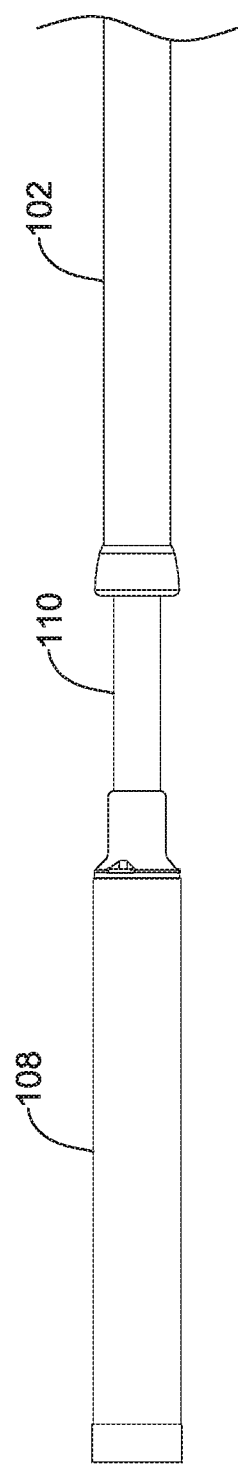

Referring briefly to FIGS. 11A and 11B, in some instances, it may be desirable to advance the device containment housing 108 and the intermediate tubular member 110 without advancing the outer tubular member 102 (i.e., telescoping the intermediate tubular member 110). For example, this may facilitate advancement of the delivery device 100 within the heart or maintain the position of the device containment housing 108 once it is placed again the heart wall. To distally advance or telescope the intermediate tubular member 110 relative to the outer tubular member 102, the second locking mechanism 132 may be actuated to "unlock" the first hub portion 126 and the second hub portion 128. As described above, a rotating retaining ring 182 may be rotated, as shown at 194, to move the second locking mechanism 132 from a locked to an unlocked configuration. Once the first locking mechanism has been unlocked, the clinician may distally advance 196 the second and third hub portions 128, 130 together to distally advance the device containment housing 108 as far as desired and/or needed. The actuation of the second and third hub portions 128, 130 may simultaneously move the intermediate tubular member 110 and the inner tubular member 116 as well. This may be done during advancement of the delivery device 100 through the vasculature, before initiating the first stage of deploying the IMD 10, and/or after the first stage of deploying the IMD 10 has been completed, as desired or needed.

After the first stage of deployment of the IMD 10, in which the tines or hooks 26 have been deployed from the device containment housing 108 into engagement with the heart wall, the tether 112 may be used to perform a tug test to determine if the IMD 10 is sufficiently engaged with the heart wall. In other words, the fixation of the IMD 10 (e.g. how well the hooks 26 are secured to the heart tissue) may be tested by gently tugging on the ends of the tether 112. If it is determined that the IMD 10 is sufficiently engaged with the heart wall, then the user may proceed to the second stage of deployment of the IMD 10 in which the remainder of the IMD 10 is expelled from the device containment housing 108. Otherwise, if the tug test fails and it is determined that the IMD 10 is not sufficiently engaged with the heart wall, the user may use the tether to pull (retract) the IMD 10, including the tines or hooks 26, back into the device containment housing 108 to release the implantable medical device 10 from the heart wall. The IMD 10 may then be repositioned and the first stage of deployment repeated.

Returning to FIG. 10B, the second stage of deploying the IMD 10 may proximally retract the device containment housing 108, and thus the intermediate tubular member 110, relative to the inner tubular member 116 to fully deploy the IMD 10. Once the clinician has determined that the position of the IMD 10 is satisfactory and the fixation mechanism 24 is securely engaged with the heart tissue, the intermediate tubular member 110, including the device containment housing 108, of the delivery device 100 can be proximally retracted. To initiate the second stage of the deployment, the clinician may first rotate the third hub portion 130, as shown at 192, such that the button 131 is aligned with the distal portion 183 of the groove 178. The clinician may then stabilize the third hub portion 130 relative to the patient and proximally retract the first and second hub portions 126, 128. It should be noted that while it is possible to distally actuate the third hub portion 130 at this point, this may cause additional and unnecessary forces to be applied to the heart wall. Further, such distal movement of the third hub portion 130 may move the inner tubular member 116 (and hence the implantable medical device 10) distally rather than proximally retracting the intermediate tubular member 110 and/or the outer tubular member 102. The first and second hub portions 126, 128 may be proximally retracted until the first locking mechanism 134 engages the distal end 181 of the groove 178, resulting in the handle assembly 120 configuration shown in FIG. 10D. Such actuation of the first and second hub portions 126, 128 may fully deploy the implantable medical device 10 such that the IMD 10 is exterior of the device containment housing 108 and engaged with the heart wall, as shown in FIG. 10E.

Figure 10E:
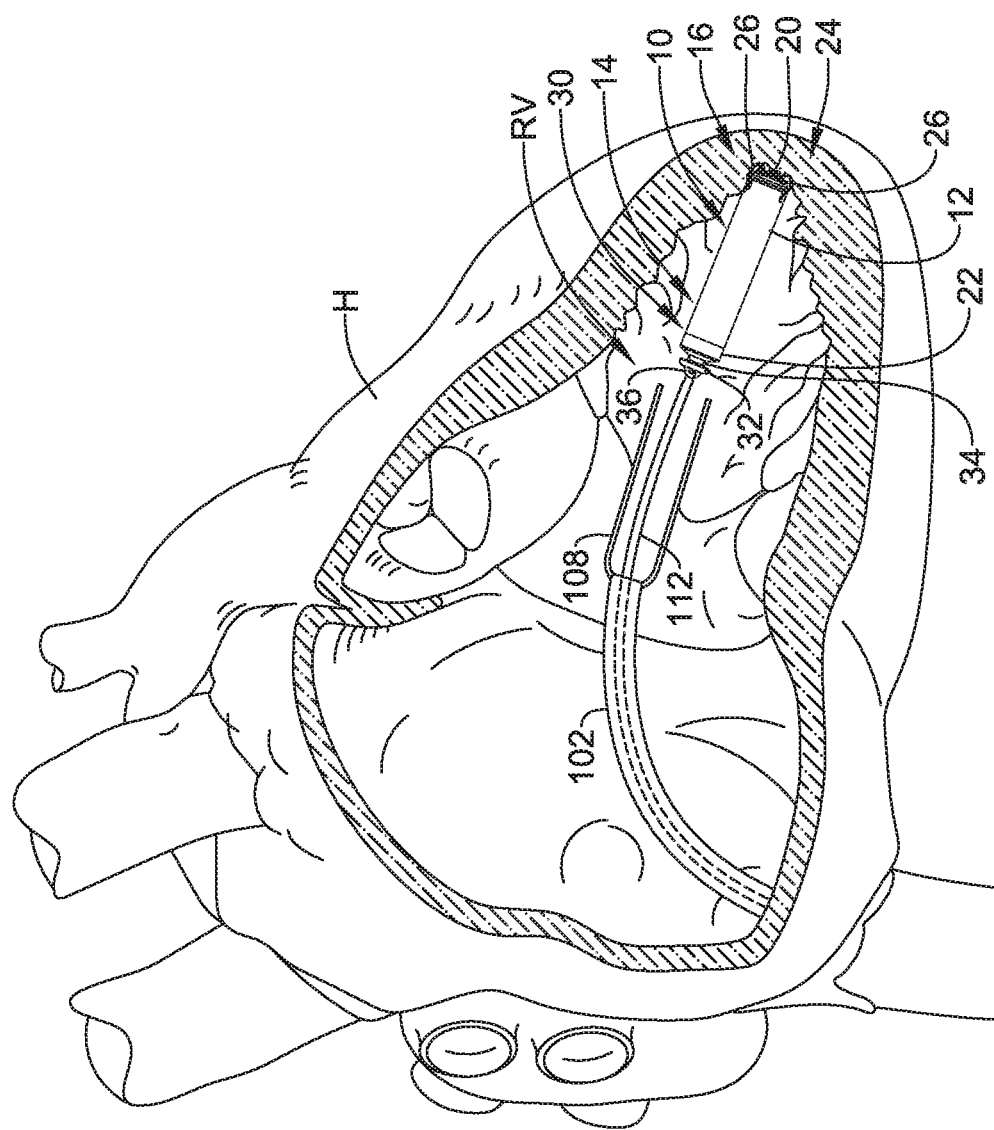

As can be seen in FIG. 10E, the IMD 10 may still be affixed to the delivery device 100 through the tether 112. Once the clinician has verified the position of the IMD 10, the fixation of the IMD 10 and/or the electrical performance of the IMD 10, the tether 112 may be removed. In some instances, fixation of the IMD 10 (e.g. how well the hooks 26 are secured to the heart tissue) may be tested by gently tugging on the ends of the tether 112. The tether 112 may be removed by unlocking the tether lock 164, removing the tether cap 166, cutting the tether 112 at some location along its length, and pulling on one of the ends until the opposite end has passed through the opening 38 of the IMD 10 such that the IMD 10 is free from the tether 112. In some instances, the tether 112 may be affixed to a portion of the tether cap 166 (e.g. creating a loop) such that the tether 112 must be cut to allow the IMD 10 to be freed from the tether 112.

In some cases, there may be a desire to test a possible implantation site before deploying and fixating the IMD 10. In some cases, a delivery device such as the delivery device 100 may include structure or otherwise be configured to be able to electrically test a possible implantation site by delivering an electrical pulse to cardiac tissue proximate the possible implantation site and measuring a resultant cardiac parameter. If the measured cardiac parameter indicates a good implantation site, the IMD 10 may be deployed and fixated at that implantation site as discussed with respect to FIGS. 10A-10E. Otherwise, the delivery device 100 may be moved to another possible site, which can then be tested. This may be repeated until an acceptable site is found. FIGS. 12-19 provide illustrative but non-limiting examples of how the delivery device 100 in general, and the device containment housing 108 in particular, may be modified to help in testing possible implantation sites.

Figure 12:
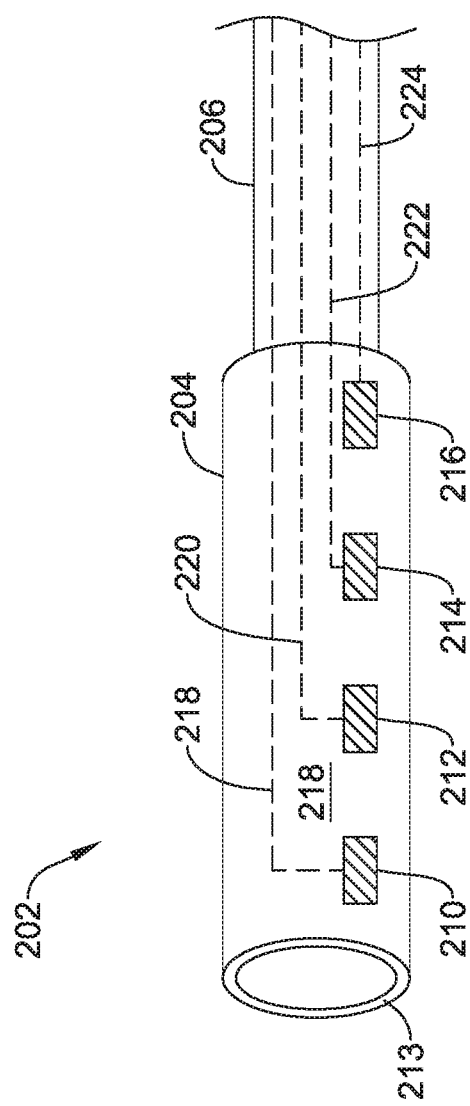
FIG. 12 is a schematic view of a distal portion of the illustrative delivery device, showing features of the device containment housing.

FIG. 12 is a schematic diagram of a portion of an illustrative delivery device 202, which may be considered as being an example of the delivery device 100. In some cases, as illustrated, the delivery device 202 includes a device containment housing 204 extending distally from a shaft 206. In some cases, the device containment housing 204 may be considered as being an example of the device containment housing 108 while the shaft 206 may be considered as generally representing at least a portion of the intermediate tubular member 110 and the outer tubular member 102, and may in some cases be considered as extending proximally to the handle assembly 120. In some cases, as seen, the device containment housing 204 includes several electrodes that may be used in electrically testing a possible implantation site. The electrodes may, for example, be disposed on an outer surface 208 of the device containment housing 204 and in some cases may be axially and/or radially spaced apart on the outer surface 208. As shown, there is a first electrode 210, a second electrode 212, a third electrode 214 and a fourth electrode 216. In some cases, one or more of the electrodes 210, 212, 214 and 216 may extend radially at least partially about the outer surface 208.

In some cases, a first electrical connector 218 extends proximally from the first electrode 210, a second electrical connector 220 extends proximally from the second electrode 212, a third electrical connector 222 extends proximally from the third electrode 214 and a fourth electrical connector 224 extends proximally from the fourth electrode 216. In some cases, the electrical connectors 218, 220, 222 and 224 extend to the handle assembly 120 and enable a device such as but not limited to a programmer or tester to be electrically coupled to the electrodes 210, 212, 214 and 216 via the electrical connectors 218, 220, 222 and 224.

In some cases, the first electrode 210 and the fourth electrode 216 may, in combination, be considered as forming a stimulation bipole. A potential difference may be applied between the first electrode 210 and the fourth electrode 216, thereby creating a voltage therebetween. In some cases, the second electrode 212 and the third electrode 214 may be used to provide a resistance measurement by detecting a voltage between the second electrode 212 and the third electrode 214 resulting from the potential difference applied between the first electrode 210 and the fourth electrode 216. In some cases, as illustrated, the second electrode 212 and the third electrode 214 may be disposed between the first electrode 210 and the fourth electrode 216. It will be appreciated that in some cases, there may be a relationship between the detected resistance between the second electrode 212 and the third electrode 214 and the current chamber volume of the corresponding chamber of the heart when a current is applied between the first electrode 210 and the fourth electrode 216. In some cases, it may be possible, for example, to use the first electrode 210 and the third electrode 214 to stimulate and to use the second electrode 212 and the fourth electrode 216 to measure conductivity, for example. In some cases, an external electrode such as a temporary patch electrode may be worn by the patient and may for example be used as part of a stimulation circuit.

In some cases, the first electrode 210 may be smaller than the fourth electrode 216. When so provided, the first electrode 210 may be the cathode and the fourth electrode 216 may be the anode of the stimulation bipole (cathodic stimulation). While not explicitly shown, in some cases the first electrode 210 may extend over the distal end 213 of the device containment housing 204 so as to directly engage tissue when the distal end 213 of the device containment housing 204 is pushed up against a heart wall.

In some cases, conductivity values obtained via electrodes on the device containment housing 204 may, for example, be used to determine heart wall contact. For example, blood has a lower conductivity compared to tissue such as cardiac tissue. A relatively lower conductivity value may indicate a lack of tissue contact while a relatively higher conductivity value may indicate tissue contact, for example. In some cases, tissue composition may impact conductivity. For example, infarcted tissue has more collagen than healthy myocardium, and thus a conductivity value may be useful in determining whether a possible implantation site includes healthy myocardium or unhealthy myocardium, which can be important in achieving lower pacing threshold values.

Figure 13:
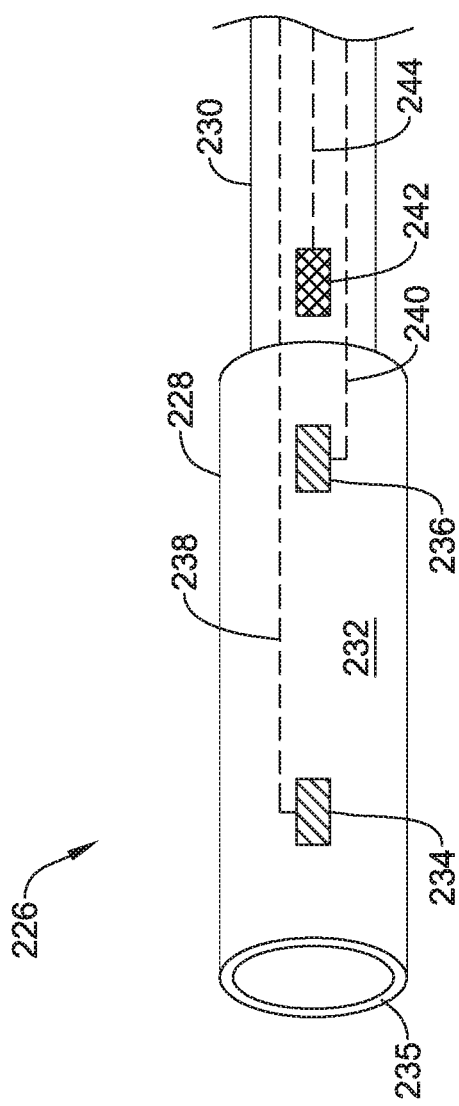
FIG. 13 is a schematic view of a distal portion of the illustrative delivery device, showing features of the device containment housing.

FIG. 13 is a schematic diagram of a portion of an illustrative delivery device 226, which may be considered as being an example of the delivery device 100. In some cases, as illustrated, the delivery device 226 includes a device containment housing 228 extending distally from a shaft 230. In some cases, the device containment housing 228 may be considered as being an example of the device containment housing 108 while the shaft 230 may be considered as generally representing at least a portion of the intermediate tubular member 110 and the outer tubular member 102, and may in some cases be considered as extending proximally to the handle assembly 120. In some cases, as seen, the device containment housing 228 includes several electrodes that may be used in electrically testing a possible implantation site. The electrodes may, for example, be disposed on an outer surface 232 of the device containment housing 228 and in some cases may be axially and/or radially spaced apart on the outer surface 232. As shown, there is a first electrode 234 and a second electrode 236 that may function together as a stimulation bipole. While not explicitly shown, in some cases the first electrode 234 may extend over the distal end 235 of the device containment housing 228 so as to directly engage tissue when the distal end 235 of the device containment housing 228 is pushed up against a heart wall. In some cases, a first electrical connector 238 extends proximally from the first electrode 234 and a second electrical connector 240 extends proximally from the second electrode 212. In some cases, the electrical connectors 238 and 240 extend to the handle assembly 120 and enable a device such as but not limited to a programmer or tester to be electrically coupled to the electrodes 234 and 236 via the electrical connectors 238 and 240.

In some cases, a sensor 242 may be disposed on the shaft 230, near to the device containment housing 228. An electrical connector 244 may extend proximally from the sensor 242 and may extend to the handle assembly 120 and thus may be operably coupled with a programmer, tester or other device. In some cases, for example, the sensor 242 may be a pressure sensor such as a piezoelectric pressure sensor and may be configured to provide a signal representative of blood pressure within a cardiac chamber that results from a stimulation pulse applied as a potential difference between the first electrode 234 and the second electrode 236, for example. In some cases, the sensor 242 may instead represent an accelerometer or an acoustic sensor that can output a signal representative of cardiac performance in response to an applied stimulation pulse (e.g. heart sounds, heart wall acceleration, etc.). In some cases, the sensor 242 may represent a gyroscope that can output a signal representative of cardiac performance (e.g. twist) in response to an applied stimulation pulse. In some cases, the sensor 242 may include electronic components to amplify, filter or otherwise condition a raw sensor signal. In some cases, the sensor 242 may be a bidirectional transducer (e.g. a bidirectional acoustic transducer to facilitate ultrasound measurements).

In some cases, rather than using electrodes on the device containment housing 228 for stimulation, one or more electrodes on the IMD 10 may instead be used to stimulate cardiac tissue (provide a pacing pulse), and the electrodes 234 and 236 may instead be used to provide a resulting conductivity value. In some cases, the IMD 10 may be used to stimulate cardiac tissue and a sensor such as the sensor 242 may be used to measure a resulting cardiac parameter. In some cases, the device containment housing 228 may not include any electrodes.

In some cases, a delivery device may include two pressure sensors. As shown for example in FIG. 14, a delivery device 250 may include a device containment housing 252 extending proximally from shaft 254, and may be considered as being an example of the delivery device 100. In some cases, the device containment housing 252 may be considered as being an example of the device containment housing 108 while the shaft 254 may be considered as generally representing at least a portion of the intermediate tubular member 110 and the outer tubular member 102, and may in some cases be considered as extending proximally to the handle assembly 120. In some cases, as seen, the device containment housing 252 has an outer surface 256 and includes the first electrode 234 and the second electrode 236. In some cases, the first electrical connector 238 extends proximally from the first electrode 234 and the second electrical connector 240 extends proximally from the second electrode 212.

In some cases, a sensor 242 may represent a first pressure sensor and a sensor 258 may represent a second pressure sensor. The sensor 242 is shown operably coupled to the electrical connector 244 while the sensor 258 is shown operably coupled to an electrical connector 260 that extends proximally from the sensor 258 and thus may be operably coupled with a programmer, tester or other device. In some cases, for example, the sensor 242 and the sensor 258 may each be piezoelectric pressure sensors, or other types of pressure sensors, and may each be configured to provide a signal representative of blood pressure within a cardiac chamber that results from a stimulation pulse applied as a potential difference between the first electrode 234 and the second electrode 236, for example. In some cases, it will be appreciated that depending on the exact position of the delivery device 250 with respect to the patient's heart, the sensor 242 and the sensor 258 may see different pressure waveforms that may be useful in determining the appropriateness of a particular possible implantation site. For example, in some cases, the sensor 242 may see an atrial pressure waveform while the sensor 258 may see a ventricular pressure waveform. These may be useful in determining an A-V delay, for example.

Figure 14:
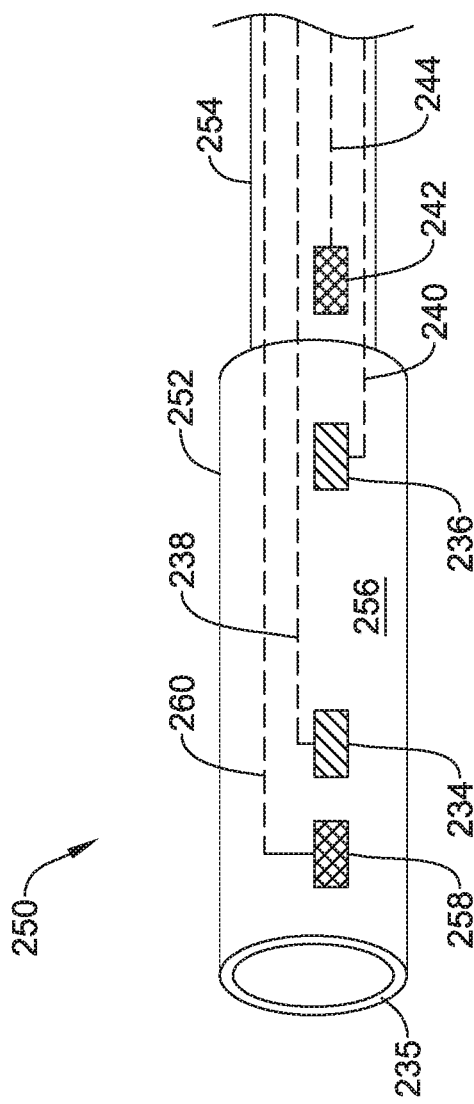
FIG. 14 is a schematic view of a distal portion of the illustrative delivery device, showing features of the device containment housing.
Figure 15:
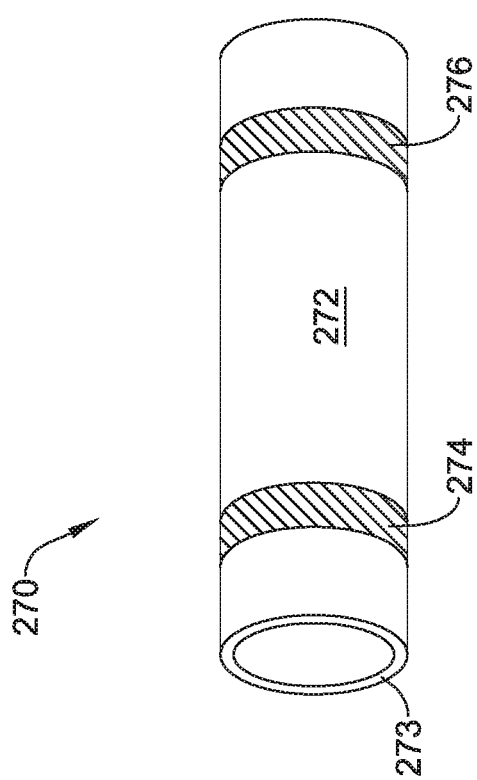
FIG. 15 is a schematic view of a distal portion of the illustrative delivery device, showing features of the device containment housing.
Figure 16:
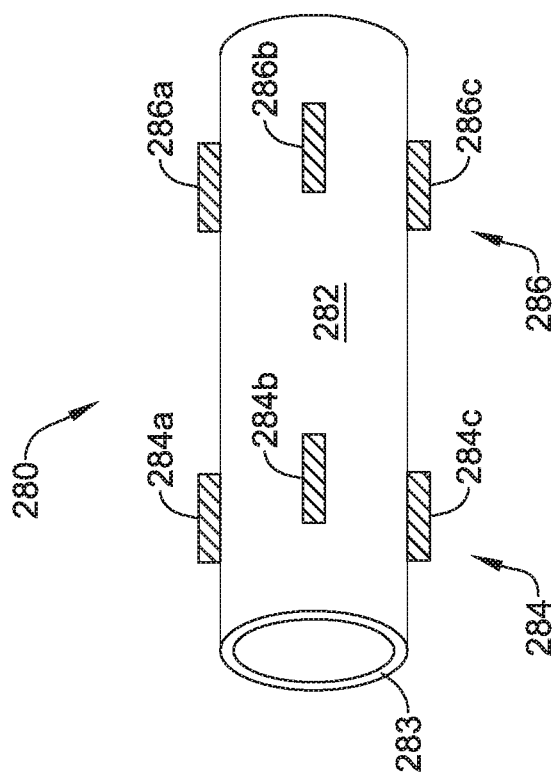
FIG. 16 is a schematic view of a distal portion of the illustrative delivery device, showing features of the device containment housing.

FIGS. 15 and 16 provide illustrative but non-limiting examples of electrode configurations that may, for example, be considered as showing possible electrode configurations useable with any of the device containment housings 204 (FIG. 12), 228 (FIG. 13) and 252 (FIG. 14). FIG. 15 shows a device containment housing 270 that has an outer surface 272. A first ring electrode 274 and a second ring electrode 276 can be seen to be disposed on the outer surface 272. It will be appreciated that by having electrodes that extend at least partially, if not entirely, around the outer surface 272, there may be fewer issues with making tissue/blood contact regardless of rotational orientation of the device containment housing 204. While not explicitly shown, in some cases the first ring electrode 274 may extend over the distal end 273 of the device containment housing 270 so as to directly engage tissue when the distal end 273 of the device containment housing 270 is pushed up against a heart wall. While two electrodes 274, 276 are shown, it will be appreciated that the device containment housing 204 may include three, four or more electrodes. In some cases, the device containment housing 204 may also include one or more sensors that are configured to provide a signal representative of cardiac performance.

FIG. 16 shows a device containment housing 280 that has an outer surface 282. A first electrode constellation 284 and a second electrode constellation 286 can be seen to be disposed on the outer surface 282. In some cases, as illustrated, the first electrode constellation 284 includes an electrode 284a, an electrode 284b and an electrode 284c. The first electrode constellation 284 may include additional electrodes not visible in this view. Similarly, the second electrode constellation 286 may include an electrode 286a, an electrode 286b and an electrode 286c. The second electrode constellation 286 may include additional electrodes not visible in this view. In some cases, each of the electrodes 284a, 284b, 284c may be electrically coupled together. In some instances, each of the electrodes 284a, 284b, 284c may be individually addressable. While not explicitly shown, in some cases each of the electrodes 284a, 284b, 284c may extend over the distal end 283 of the device containment housing 280 so as to directly engage tissue when the distal end 283 of the device containment housing 280 is pushed up against a heart wall. In some cases, each of the electrodes 286a, 286b, 286c may be electrically coupled together. In some instances, each of the electrodes 286a, 286b, 286c may be individually addressable.

It will be appreciated that by having electrodes that extend at least partially, if not entirely, around the outer surface 282, there may be fewer issues with making tissue/blood contact regardless of rotational orientation of the device containment housing 280 relative to the heart H. While two electrode constellations 284, 286 are shown, it will be appreciated that the device containment housing 280 may include three, four or more electrode constellations. In some cases, the device containment housing 280 may also include one or more sensors that are configured to provide a signal representative of cardiac performance.

Figure 17:
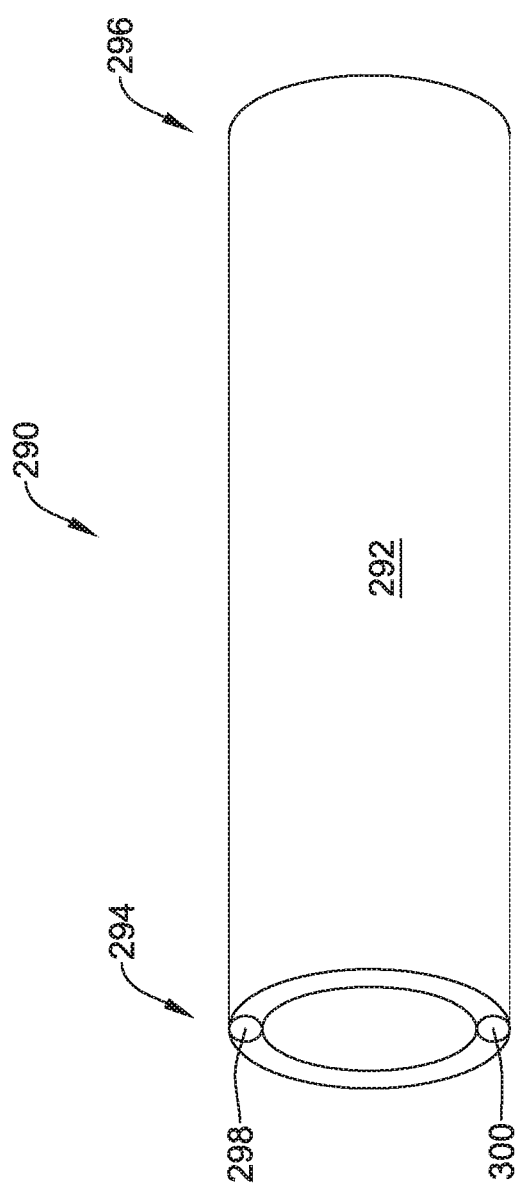
FIG. 17 is a schematic view of a distal portion of the illustrative delivery device, showing features of the device containment housing.

FIG. 17 is a schematic illustration of a device containment housing 290 including features that may be combined with any of the device containment housings 204 (FIG. 12), 228 (FIG. 13) and 252 (FIG. 14). The illustrative device containment housing 290 includes an outer surface 292 that extends from a distal end 294 to a proximal end 296. In some cases, the device containment housing 290 may include a vision system that enables a physician or other user to actually visualize a possible implantation site. A vision system may, for example, utilize intracardiac ultrasound, infrared imaging, direction vision, and the like. The distal end 294 includes a first visualization element 298 and a second visualization element 300. One these elements may, for example, be or otherwise include a light source while the other element includes a camera, or a fiber optic cable and a lens operably coupled to a proximally located camera for visualization.

Figure 18:
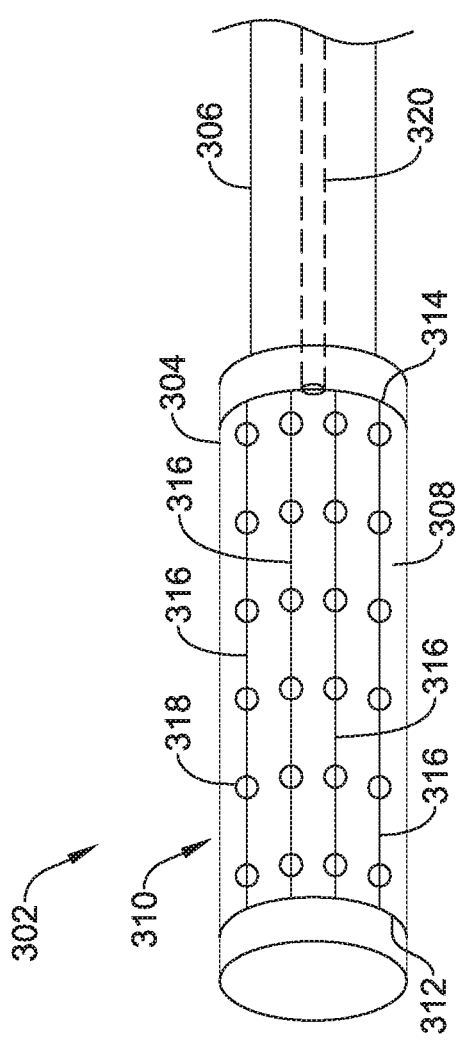
FIG. 18 is a schematic view of a distal portion of the illustrative delivery device, showing features of the device containment housing.
Figure 19:
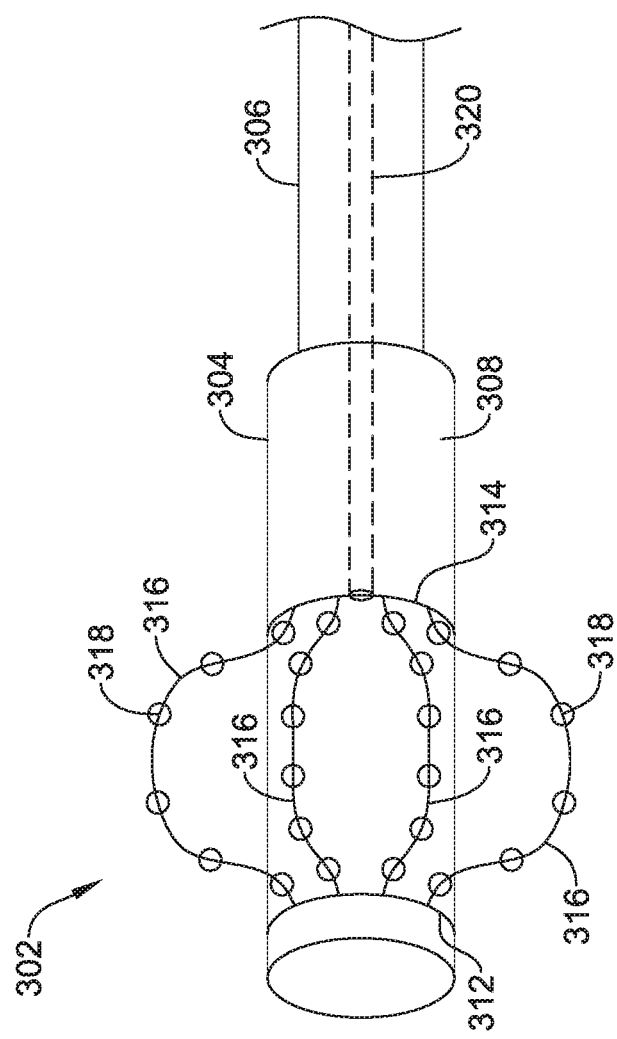
FIG. 19 is a schematic view of a distal portion of the illustrative delivery device, showing features of the device containment housing.

FIGS. 18 and 19 are schematic illustrations of a portion of a delivery device 302, which may be considered as being an example of the delivery device 100, with FIG. 18 showing the delivery device 302 in a delivery configuration while FIG. 19 shows the delivery device 302 in a mapping configuration. In some cases, as illustrated, the delivery device 302 may include a device containment housing 304 extending distally from a shaft 306. In some cases, the device containment housing 304 may be considered as being an example of the device containment housing 108 while the shaft 306 may be considered as generally representing at least a portion of the intermediate tubular member 110 and the outer tubular member 102, and may in some cases be considered as extending proximally to the handle assembly 120. In some cases, as seen, the device containment housing 304 includes electrodes that may be used in electrically testing a possible implantation site.

In some cases, the device containment housing 304 includes an electrode assembly 310 that includes a distal ring 312 and a proximal ring 314, with a plurality of electrode supports 316 extending between the distal ring 312 and the proximal ring 314. Each of the plurality of electrode supports 316 include a plurality of individually addressable electrodes 318. In some cases, the distal ring 312 is secured relative to the device containment housing 304 while the proximal ring 314 may be slidable relative to the device containment housing 304. In some cases, a deployment member 320 may be operably coupled to the proximal ring 314 and extend proximally through the shaft 306 such that the proximal ring 314 may be moved forwards and backwards by pushing and pulling on the deployment member 320. In other cases, the distal ring 312 may be slidable, and the deployment member 320 may instead be operably coupled to the distal ring 312. In either case, in the deployed state, stimulation pulses (e.g. pacing pulses) may be sequentially applied to each of the plurality of individually addressable electrodes 318, and a response may be sensed and recorded. This may help determine a suitable implantation site for the IMD. Once a suitable implantation site has been determined, the deployment member 320 may be moved to retract the electrode supports 316, and the device containment housing 304 may be positioned over the suitable site and the IMD in the device containment housing 304 may be deployed and implanted at the site.

It will be appreciated that the electrode assembly 310 permits mapping of the endocardial surface. In some cases, this may be useful in determining or otherwise identifying intrinsic activation patterns. In some cases, mapping the endocardial surface may facilitate identification of scar tissue and possibly other damaged tissue, to be avoided when deploying the IMD 10. It will be appreciated that while no sensors are shown as being part of the delivery device 302, one or more sensors such as pressure sensors, accelerometers and/or gyroscopes may be included as part of the delivery device 302 in order to gauge cardiac response to an applied stimulation via each of two or more of the individually addressable electrodes 318, for example.

As noted with respect to FIG. 2, in some cases the IMD 10 may include one or more magnetic tracking sensors and/or impedance tracking sensors. FIG. 20 schematically illustrates a system 400 in which a patient P, including a heart H, is placed in front of (or on top of) a magnetic field generator 402. In some cases, a device disposed within the heart H includes a magnetic tracking sensor and/or an impedance tracking sensor 404. In some cases, when the magnetic field generator 402 is generating a magnetic field, and the magnetic tracking sensor 404 within the device is turned on, the magnetic tracking sensor 404 is able to determine its location relative to the magnetic field lines, and to communicate this information for display on a monitor 406. When a current generator (not shown) provides current to the body (e.g. via two or more electrode patches), an impedance tracking sensor within the device may be able to determine its location relative to the electric field lines, and to communicate this information for display on a monitor 406. In some cases, both magnetic tracking and impedance tracking may be used to identify and track the location of the device. In some cases, the device including the magnetic tracking sensor and/or an impedance tracking sensor 404 may be a leadless cardiac pacemaker (LCP) or other intracardially implanted device, and the system 400 may provide an indication of the location of the device within the body. In some cases, the device including the magnetic tracking sensor and/or impedance tracking sensor 404 may instead be a delivery device, and the magnetic tracking sensor and/or an impedance tracking sensor 404 may provide an indication of the location of the delivery device. In some cases, the magnetic tracking sensor and/or impedance tracking sensor 404 may not only provide location (X, Y, Z), but may also provide pitch, yaw, velocity, acceleration, twist, and/or other parameters related to the device's position.

As illustrated, the system 400 may be a structure that the patient P lies on, or perhaps stands in front of. In some cases, it is contemplated that the magnetic field generator 402 may be incorporated into a wearable vest that may be used for ambulatory measurements. In some cases, information provided by the system 400 may be used to help guide initial implantation and to verify fixation of the device (such as the IMD 10). In some cases, the data provided may be used for determining rate response sensor calibration, as otherwise heart motion can interfere with detecting physical movement of the patient. In some cases, a co-implanted device such as but not limited to a subcutaneous implantable cardioverter-defibrillator (SICD) may be used to generate the magnetic field and/or electric field (e.g. current). In some cases, the SICD may inject a current, which may be detected by the IMD 10 and this information may be used to improve location detection via impedance tracking.

The delivery device 100, 202, 226, 250, 302, or components thereof, may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the delivery device 100, 202, 226, 250, 302, or components thereof, may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100, 202, 226, 250, 302 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100, 202, 226, 250, 302, or components thereof, to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A delivery and deployment device configured to deliver an implantable medical device (IMD) to a chamber of a patient's heart and deploy the IMD therein, the delivery and deployment device comprising:
   a handle assembly;
   a shaft extending distally from the handle assembly, the shaft including a distal region;
   a device containment housing coupled to the distal region of the shaft and extending distally therefrom, the device containment housing configured to accommodate at least part of the IMD therein;
   a plurality of electrodes distributed about an exterior surface of the device containment housing such that at least some of the plurality of electrodes may be positioned to test a potential IMD deployment location defined by the device containment housing before deploying the IMD; and
   a plurality of electrical conductors operably coupled with the plurality of electrodes and extending proximally back along the shaft toward the handle assembly, the plurality of electrical conductors having proximal ends configured to be operably coupled to a testing device, wherein the testing device is configured to deliver electrical stimulation pulses to the at least some of the plurality of electrodes to test the potential IMD deployment location defined by the device containment housing before deploying the IMD.

2. The delivery and deployment device of claim 1, wherein the plurality of electrodes include at least some electrodes that are radially disposed about the exterior surface of the device containment housing.

3. The delivery and deployment device of claim 1, wherein the plurality of electrodes comprise at least four electrodes spaced axially along the exterior surface of the device containment housing, the at least four electrodes including a first electrode, a second electrode, a third electrode and a fourth electrode;
   the first electrode and the fourth electrode spaced apart a first distance to form a stimulation dipole providing a potential difference;
   the second electrode and the third electrode spaced apart a second distance less than the first distance to provide a conductivity measurement by measuring a voltage between the second electrode and the third electrode resulting from the potential difference applied by the first electrode and the second electrode; and
   the second electrode and the third electrode disposed between the first electrode and the fourth electrode.

4. The delivery and deployment device of claim 1, wherein the plurality of electrodes comprise a first electrode and a second electrode disposed on an exterior surface of the device containment housing to form a stimulation bipole.

5. The delivery and deployment device of claim 4, further comprising a pressure sensor configured to obtain an indication of pressure in the chamber of the patient's heart in response to a stimulating electrical pulse delivered via the first electrode and the second electrode.

6. The delivery and deployment device of claim 5, wherein the pressure sensor is disposed at or near a proximal end of the device containment housing.

7. The delivery and deployment device of claim 4, further comprising:
   a first pressure sensor configured to obtain an indication of pressure in the chamber of the patient's heart; and
   a second pressure sensor configured to obtain an indication of pressure in a different chamber of the patient's heart.

8. The delivery and deployment device of claim 4, further comprising an accelerometer and/or a gyroscope operatively fixed to the device containment housing, the accelerometer and/or the gyroscope are configured to output a signal to the testing device representative of cardiac performance.

9. The delivery and deployment device of claim 1, wherein at least some of the plurality of electrodes are disposed on an expandable assembly movably secured about an exterior of the device containment housing, the expandable assembly movable to a deployed configuration in which at least some of the plurality of electrodes contact cardiac tissue for endocardial mapping of at least part of the chamber of the patient's heart prior to IMD deployment.

10. The delivery and deployment device of claim 1, further comprising one or more magnet tracking sensor fixed relative to the device containment housing for tracking purposes.

11. An IMD implantation device configured to deliver an implantable medical device (IMD) to a chamber of a patient's heart and deploy the IMD therein, the IMD implantation device comprising:
   a handle assembly;
   a shaft extending distally from the handle assembly, the shaft including a distal region;
   a device containment housing coupled to the distal region of the shaft and extending distally therefrom, the device containment housing configured to accommodate at least part of the IMD therein;
   a deployment member extending through the shaft, the deployment member configured to apply a deployment force to the IMD in order to move the IMD from the device containment housing to deploy the IMD in the patient's heart;
   a plurality of electrodes distributed about an exterior surface of the device containment housing such that at least some of the plurality of electrodes may be positioned to test a potential IMD deployment location defined by the device containment housing before deploying the IMD; and
   a plurality of electrical conductors operably coupled with the plurality of electrodes and extending proximally back along the shaft toward the handle assembly, the plurality of electrical conductors having proximal ends configured to be operably coupled to a testing device, wherein the testing device is configured to deliver electrical stimulation pulses to the at least some of the plurality of electrodes to test the potential IMD deployment location defined by the device containment housing before deploying the IMD.

12. The IMD implantation device of claim 11, wherein the deployment member is a push tube, and wherein the IMD implantation device further comprises:
   a tether extending distally through the push tube and coupled to the IMD, the tether configured to be used to retrieve the IMD back into the device containment housing if an alternate deployment location is desired.

13. The IMD implantation device of claim 12, wherein the plurality of electrodes comprise at least four electrodes spaced axially along the device containment housing, the at least four electrodes including a first electrode, a second electrode, a third electrode and a fourth electrode;
- the first electrode and the fourth electrode are spaced apart a first distance to form a stimulation dipole providing a potential difference, wherein the fourth electrode extends to a distal end of the device containment housing;
- the second electrode and the third electrode are spaced apart a second distance less than the first distance to provide a conductivity measurement by measuring a voltage between the second electrode and the third electrode resulting from the potential difference applied by the first electrode and the second electrode; and
- the second electrode and the third electrode disposed between the first electrode and the fourth electrode.

14. The IMD implantation device of claim 11, wherein the plurality of electrodes comprise a first electrode and a second electrode disposed on an exterior surface of the device containment housing to form a stimulation bipole.

15. The IMD implantation device of claim 14, further comprising a pressure sensor configured to obtain an indication of pressure in the chamber of the patient's heart in response to a stimulating electrical pulse delivered via the first electrode and the second electrode.

16. The IMD implantation device of claim 15, wherein the pressure sensor is disposed at or near a proximal end of the device containment housing.

17. The IMD implantation device of claim 14, further comprising an accelerometer and/or a gyroscope fixed relative to the device containment housing.

* * * * *